US011357640B2

(12) United States Patent
Weiman et al.

(10) Patent No.: US 11,357,640 B2
(45) Date of Patent: Jun. 14, 2022

(54) EXPANDABLE INTERBODY FUSIONS DEVICES

(71) Applicant: GLOBUS MEDICAL, INC., Audubon, PA (US)

(72) Inventors: Mark Weiman, Downingtown, PA (US); Myles Sullivan, Philadelphia, PA (US); Tyler Hessler, Phoenixville, PA (US); Chad Glerum, Pennsburg, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 16/923,362

(22) Filed: Jul. 8, 2020

(65) Prior Publication Data

US 2022/0008212 A1 Jan. 13, 2022

(51) Int. Cl.
*A61F 2/44* (2006.01)
*A61F 2/30* (2006.01)

(52) U.S. Cl.
CPC ............ *A61F 2/4425* (2013.01); *A61F 2/447* (2013.01); *A61F 2002/30405* (2013.01); *A61F 2002/443* (2013.01)

(58) Field of Classification Search
CPC ...... A61F 2/44–447; A61F 2002/30405; A61F 2002/443
See application file for complete search history.

(56) References Cited

U.S. PATENT DOCUMENTS

| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |

(Continued)

FOREIGN PATENT DOCUMENTS

| CA | 2088066 A1 | 1/1992 |
| DE | 4012622 C1 | 7/1991 |

(Continued)

*Primary Examiner* — Nicholas J Plionis

(57) ABSTRACT

Expandable fusion devices, systems, instruments, and methods thereof. The expandable fusion implant may include an upper endplate assembly and a lower endplate assembly. The upper and lower endplate assemblies may be configured to expand in width. A rotatable actuator may move one or more driving ramps, which mate with an upper ramp and a lower ramp, respectively. The actuator may cause independent movement of one or more of the driving ramps, thereby causing an expansion in height of the upper and lower endplate assemblies.

11 Claims, 19 Drawing Sheets

(56) References Cited

U.S. PATENT DOCUMENTS

| | | |
|---|---|---|
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | Jimenez et al. |
| 9,532,883 B2 | 1/2017 | McLuen et al. |
| 9,622,878 B2 | 4/2017 | Grotz |
| 10,105,238 B2 * | 10/2018 | Koch ............... A61F 2/44 |
| 2002/0045945 A1 | 4/2002 | Liu |
| 2002/0068976 A1 | 6/2002 | Jackson |
| 2002/0068977 A1 | 6/2002 | Jackson |
| 2004/0030387 A1 | 2/2004 | Landry |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte |
| 2005/0113916 A1 | 5/2005 | Branch, Jr. |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish et al. |
| 2006/0015184 A1 | 1/2006 | Winterbottom |
| 2006/0058878 A1 | 3/2006 | Michelson |
| 2006/0084986 A1 | 4/2006 | Grinberg |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote |
| 2008/0140207 A1 * | 6/2008 | Olmos ............ A61B 17/025 623/17.16 |
| 2008/0147194 A1 | 6/2008 | Grotz |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0076616 A1 | 3/2009 | Duggal |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 * | 12/2009 | McCormack ...... A61B 17/8822 606/83 |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger |
| 2010/0286783 A1 | 11/2010 | Lechmann |
| 2011/0035011 A1 | 2/2011 | Cain |
| 2011/0093074 A1 | 4/2011 | Glerum |
| 2011/0160861 A1 | 6/2011 | Jimenez |
| 2011/0172774 A1 | 7/2011 | Varela |
| 2011/0276142 A1 | 11/2011 | Niemiec |
| 2011/0301713 A1 | 12/2011 | Theofilos |

(56) References Cited

U.S. PATENT DOCUMENTS

| | | |
|---|---|---|
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0265309 A1 | 10/2012 | Glerum |
| 2012/0277861 A1 | 11/2012 | Steele et al. |
| 2012/0277870 A1 | 11/2012 | Wolters |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1 | 1/2013 | Glerum |
| 2013/0085572 A1* | 4/2013 | Glerum ............ A61F 2/44 623/17.16 |
| 2013/0158669 A1 | 6/2013 | Sungarian |
| 2013/0274883 A1 | 10/2013 | McLuen et al. |
| 2014/0088714 A1 | 3/2014 | Miller et al. |
| 2014/0100658 A1* | 4/2014 | Schmura ............ A61F 2/4425 623/17.15 |
| 2014/0236297 A1* | 8/2014 | Iott ............ A61F 2/4611 623/17.15 |
| 2015/0066145 A1 | 3/2015 | Rogers et al. |
| 2015/0088258 A1 | 3/2015 | Jimenez et al. |
| 2015/0100128 A1* | 4/2015 | Glerum ............ A61F 2/447 623/17.16 |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2016/0338846 A1* | 11/2016 | Walker ............ A61F 2/4611 |
| 2017/0100258 A1 | 4/2017 | Jimenez et al. |
| 2017/0119543 A1 | 5/2017 | Dietzel et al. |
| 2019/0008654 A1 | 1/2019 | Thommen et al. |
| 2019/0269521 A1* | 9/2019 | Shoshtaev ............ A61F 2/447 |
| 2019/0388232 A1* | 12/2019 | Purcell ............ A61F 2/442 |
| 2020/0163775 A1 | 5/2020 | Kim et al. |
| 2021/0137695 A1* | 5/2021 | Huang ............ A61F 2/447 |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| WO | 9201428 A1 | 2/1992 |
| WO | 9525485 A1 | 9/1995 |
| WO | 199942062 A1 | 8/1999 |
| WO | 199966867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2012031267 A1 | 3/2012 |
| WO | 2014164625 A1 | 10/2014 |
| WO | 2017004503 A1 | 1/2017 |

* cited by examiner

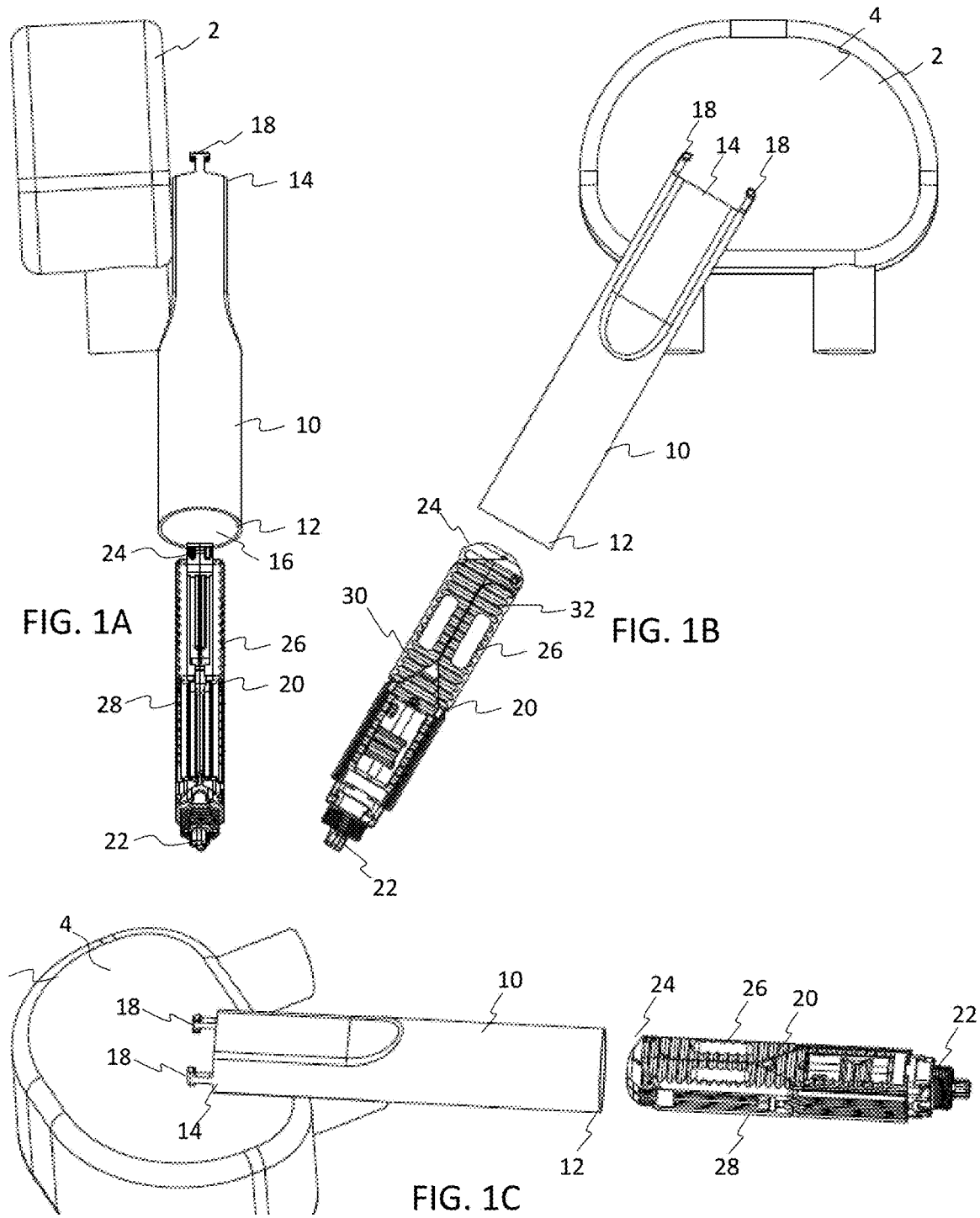

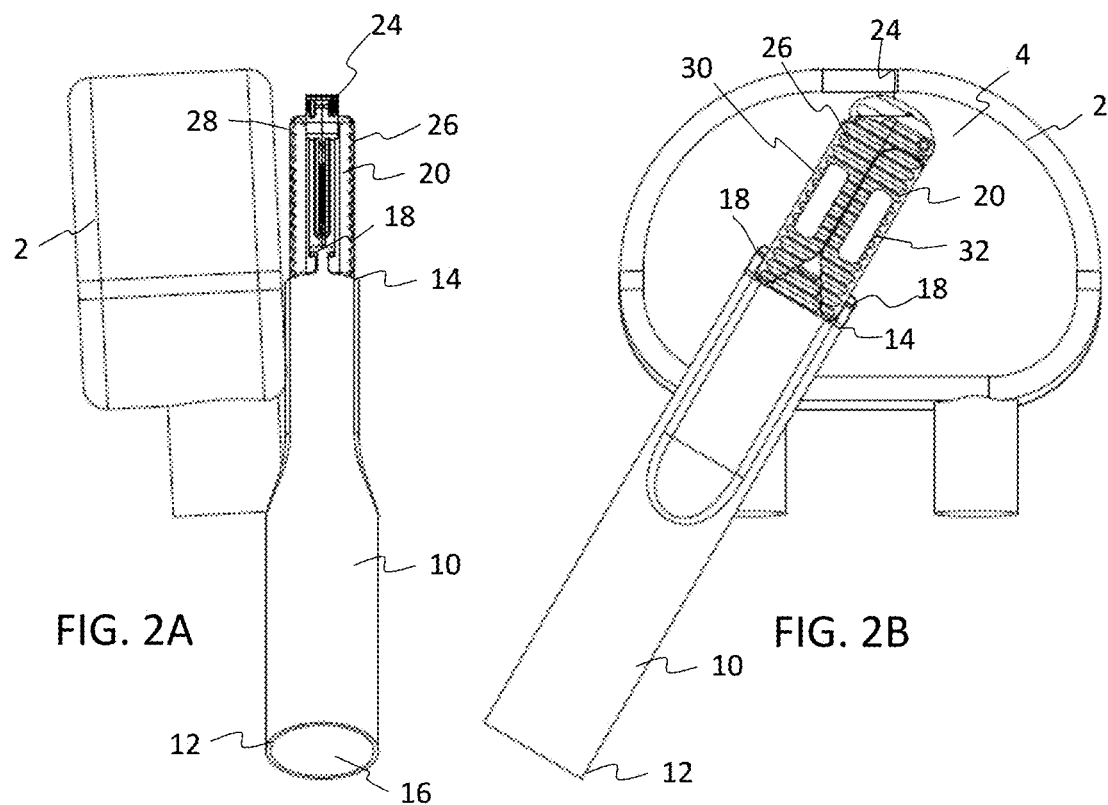
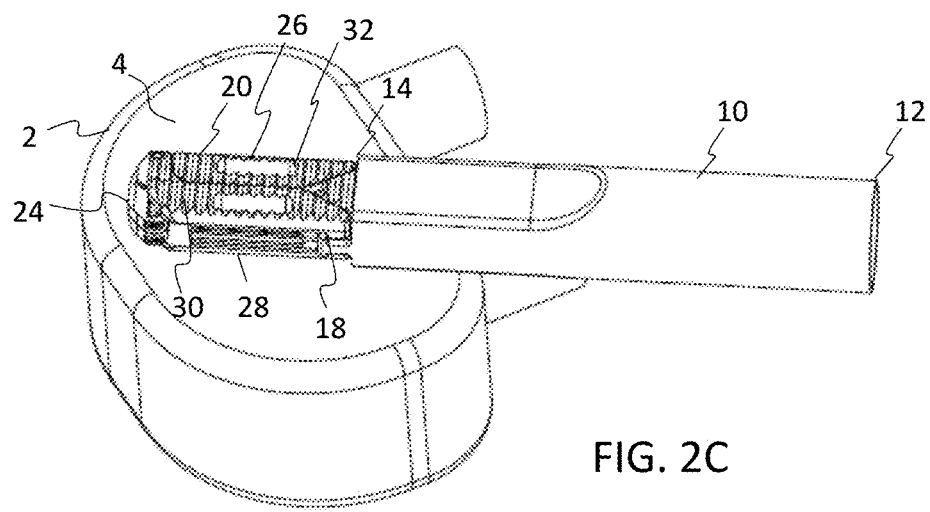
FIG. 2A
FIG. 2B
FIG. 2C

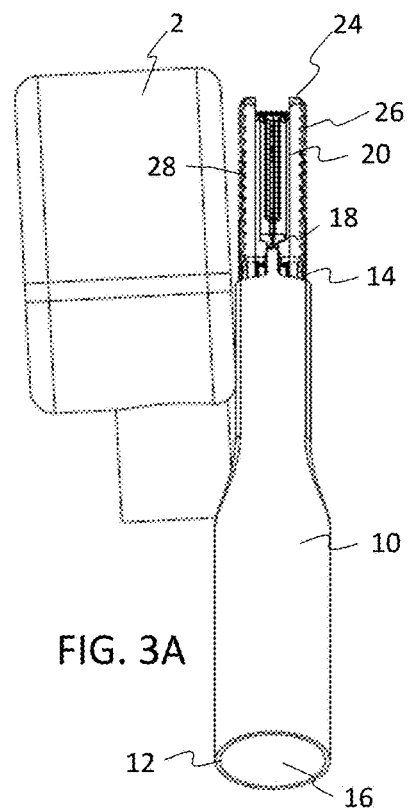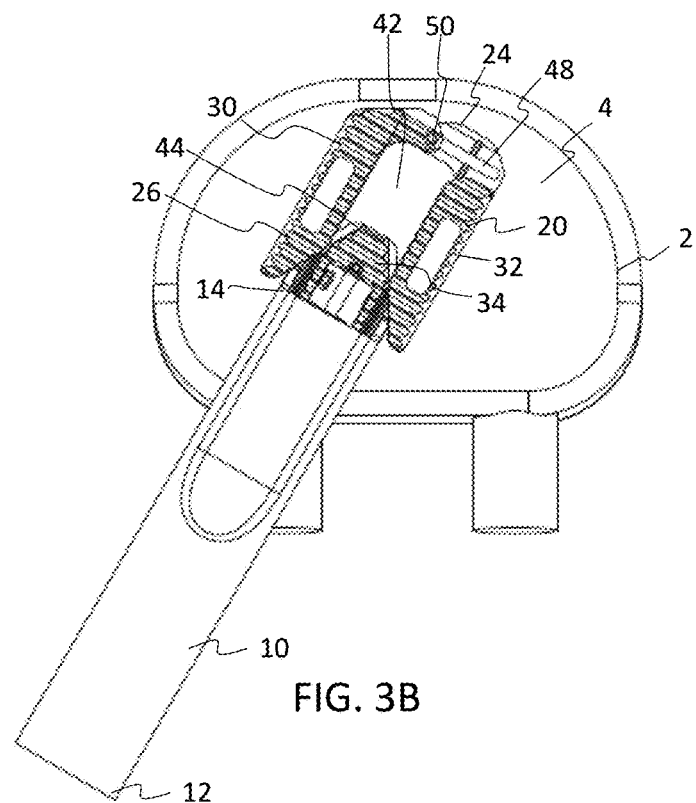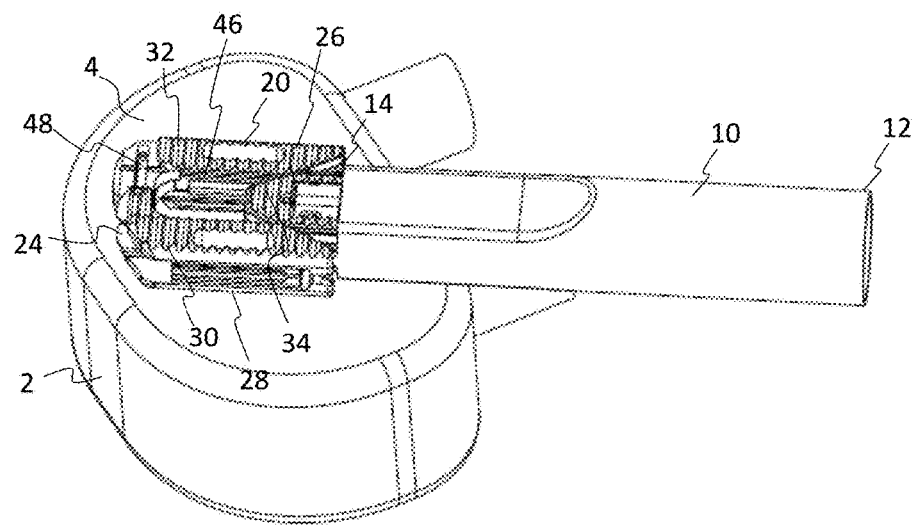

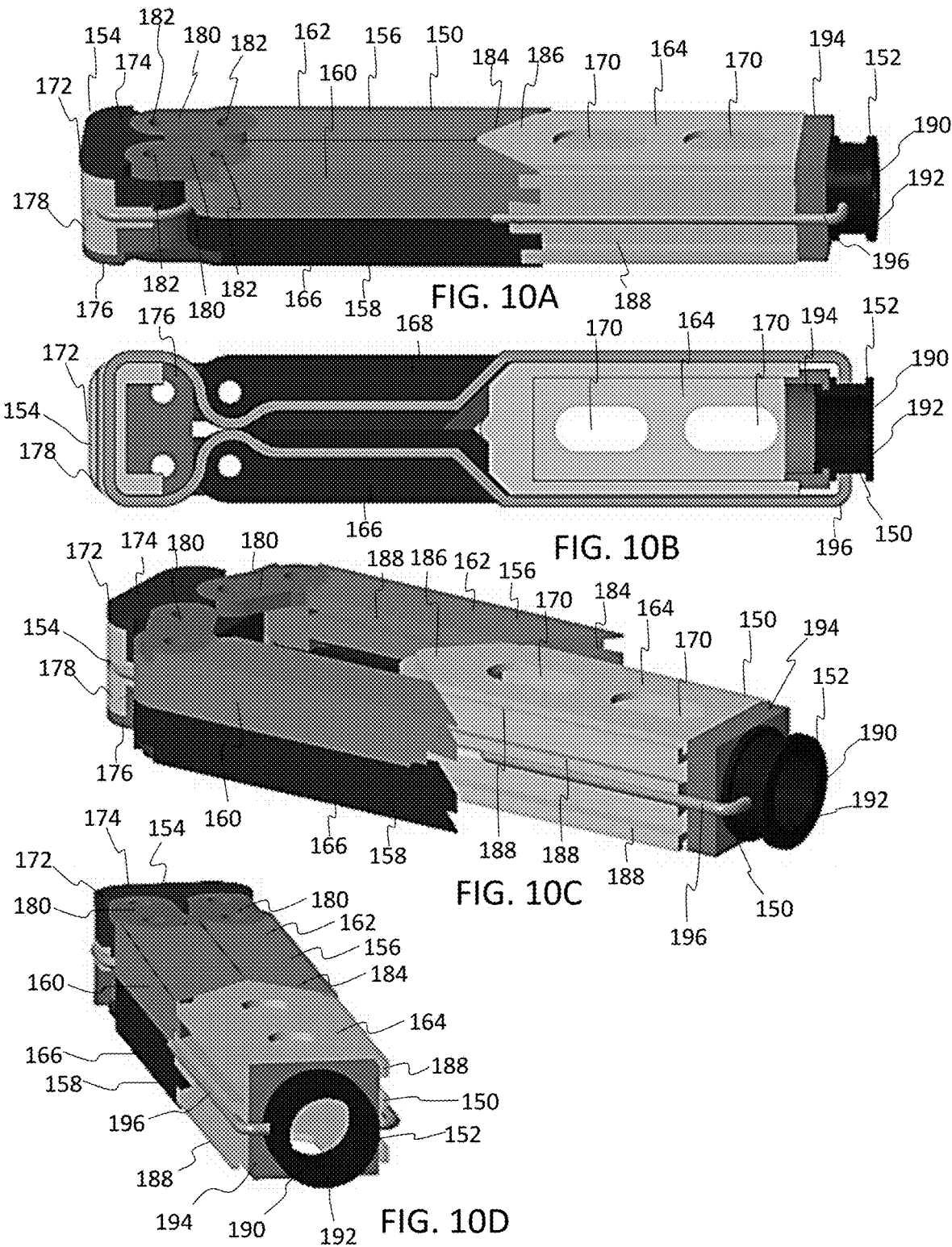

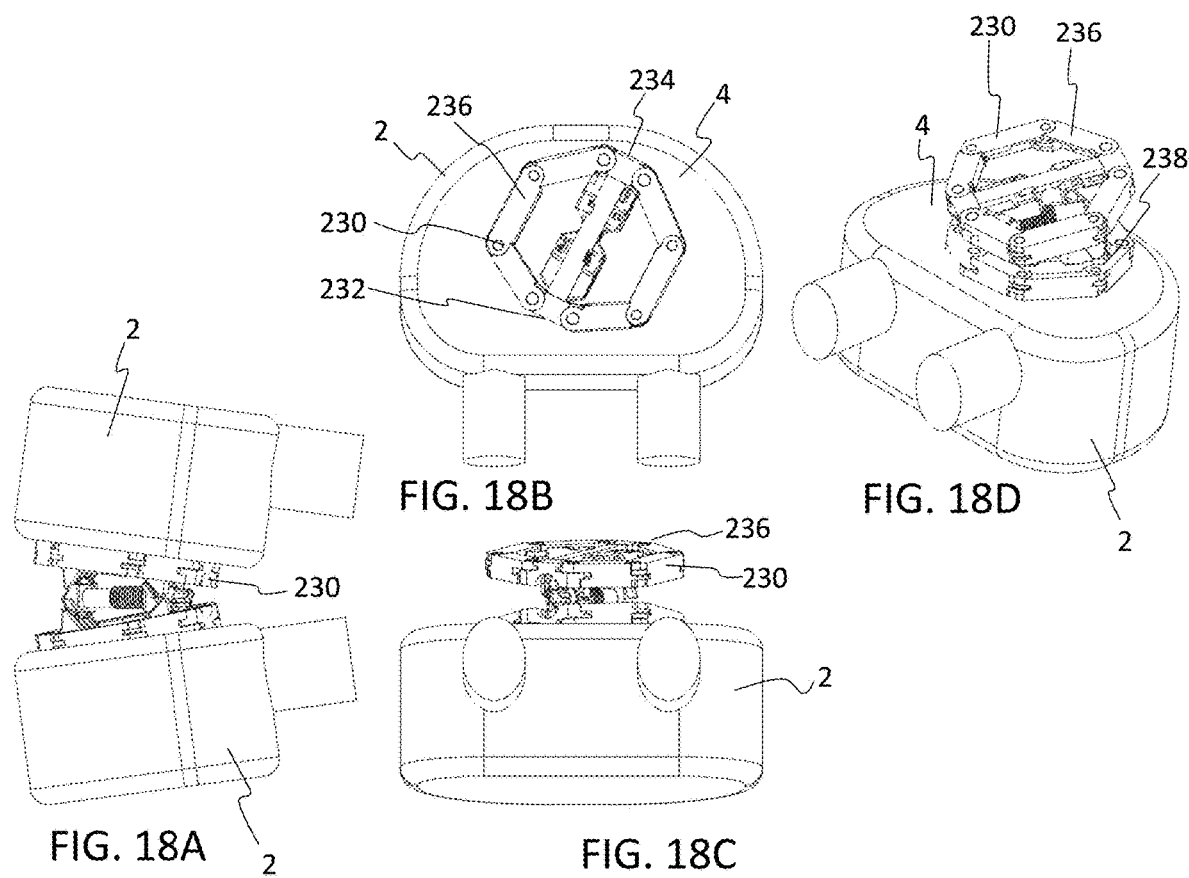

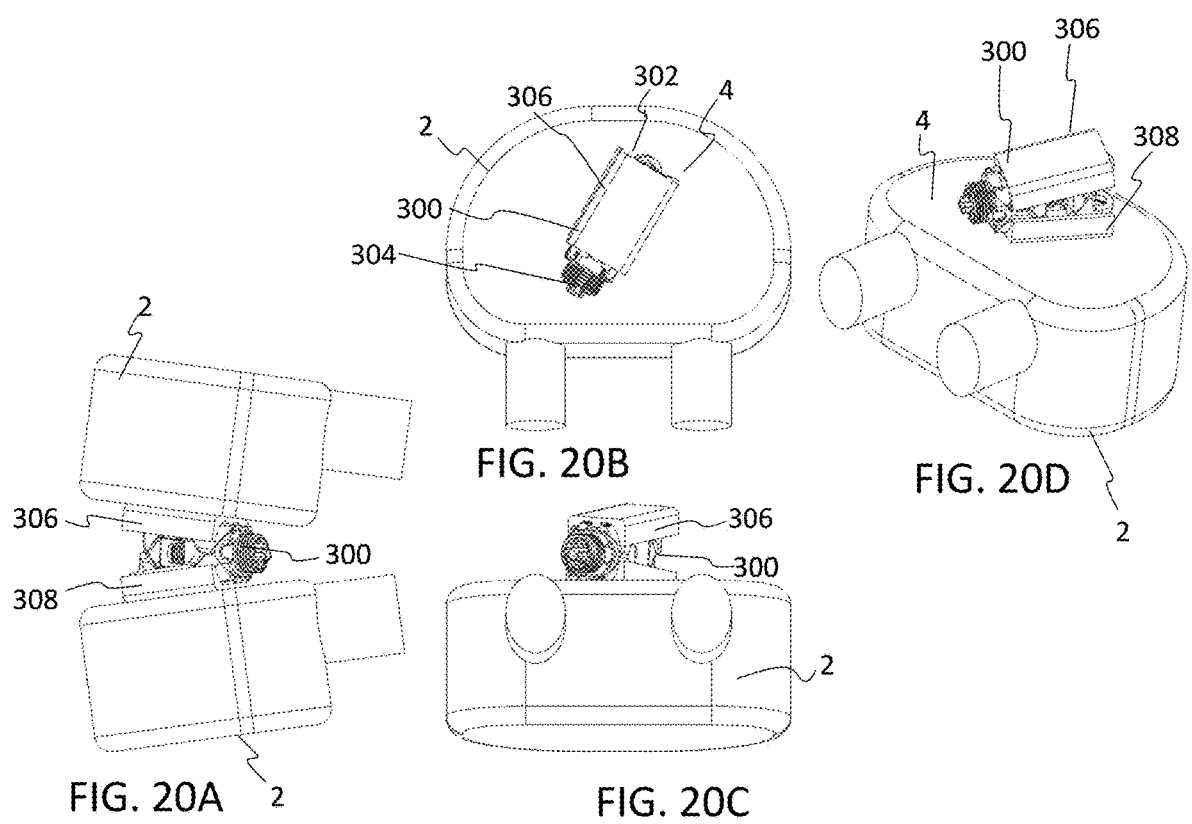

EXPANDABLE INTERBODY FUSIONS DEVICES

FIELD OF THE INVENTION

The present disclosure relates to surgical devices, and more particularly, to expandable fusion devices capable of being deployed inside an intervertebral disc space and then expanded in width and/or in height to maintain disc spacing, restore spinal stability, and/or facilitate an intervertebral fusion.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

Interbody devices have been used to provide support and stability in the anterior column of the spinal vertebrae when treating a variety of spinal conditions, including degenerative disc disease and spinal stenosis with spondylolisthesis. Clinical treatment of spinal pathologies with anterior vertebral body interbody devices relies on precise placement of the interbody device to restore normal anterior column alignment. Iatrogenic pathologies may result from the surgical access window to the disc space, failure to precisely place the interbody on hard cortical bone often found on the apophyseal ring of the vertebral body, and/or failure to precisely control and restore normal anatomical spinal alignment.

As such, there exists a need for a fusion device capable of precise placement of interbody support that both increases interbody contact with hard cortical bone and provides precise control of anterior column alignment while reducing the profile of the access window to the disc space.

SUMMARY OF THE INVENTION

To meet this and other needs, and in view of its purposes, the present application provides devices, systems, instruments, and methods for installing, and expanding the interbody implant in width and/or height. In particular, an expandable fusion device is provided, which has a narrow profile and may expand in width to increase surface area contact and/or has a reduced height and may expand in height to restore anatomical spinal alignment. The expandable fusion device may have the ability to individually adjust the anterior and posterior heights of the interbody and to adjust sagittal balance correction. The device may be installed in an open, semi-open, or minimally invasive surgical procedure. The expandable fusion device may be capable of being placed into the disc space down a guide tube or cannula, for example, widened in width, and then expanded in height into an expanded configuration. The implant may also be configured to passively pivot about a longitudinal axis of the implant. The passive adjustment of the endplates may account for the mismatch of the oblique angle of insertion and/or the desired sagittal angle According to one embodiment, an expandable implant includes an upper endplate assembly, a lower endplate assembly, an actuator assembly, a plurality of driving ramps, and upper and lower ramps mated with the driving ramps. The upper endplate assembly may include a plurality of upper endplates. The lower endplate assembly may include a plurality of lower endplates. The actuator assembly may include a rotatable actuator having a shaft and a rotatable nut. The plurality of driving ramps may include a front ramp, a mid-ramp, and a rear ramp positioned along the shaft of the actuator. The upper ramp may be connected to the upper endplate assembly and engaged with the plurality of driving ramps. The lower ramp may be connected to the lower endplate assembly and engaged with the plurality of driving ramps. The upper and lower endplate assemblies may be configured to expand in width. Rotation of the actuator and/or the nut may cause movement of one or more of the driving ramps, which press against the upper and lower ramps, thereby causing an expansion in height of the upper and lower endplate assemblies.

In one embodiment, the plurality of upper endplates may include a first upper outer endplate, a second upper outer endplate, and a third upper central endplate positionable between the first and second upper outer endplates. The plurality of lower endplates may include a first lower outer endplate, a second lower outer endplate, and a third lower central endplate positionable between the first and second lower outer endplates. The upper and lower central endplates may be configured to expand the respective upper and lower outer endplates outwardly, thereby expanding the overall width of the implant. One of the outer endplates may include an elongate groove and the other outer endplate may retain a pin configured to be received within the elongate groove such that when the outer endplates move outwardly, the pin is guided along the path of the elongate groove. For example, the elongate groove may be a linear groove that allows for a generally parallel expansion in width of the outer endplates. The central endplates may be configured to slide between the outer endplates on one or more tracks. When the central endplate is advanced forward distally along the one or more tracks, the outer endplates expand in width.

The height of the implant may be expanded by an actuation assembly. The shaft of the actuator may include a first threaded portion, a second threaded portion, and a non-threaded portion. The front driving ramp may be positioned on the non-threaded portion of the actuator, the mid-ramp may be positioned on the first threaded portion, and the rear ramp may be positioned on the second threaded portion. The first and second threaded portions may have different attributes, such as different outer diameters, handedness, thread form, thread angle, lead, pitch, etc. For example, the first threaded portion may have a smaller outer diameter and different handedness than the second threaded portion. The rotatable nut may be configured to move the rear ramp independent of the mid-ramp and front ramp.

The upper and lower endplate assemblies may be configured to passively pivot about a longitudinal axis of the implant. For example, the outer surfaces of the upper and lower ramps may each define one or more slots configured to guide one or more corresponding tabs on the inner cavities of the upper and lower central endplates, respectively. The slot may include a circular t-slot configured to guide or pivot the central endplates about the longitudinal axis of the implant. In this manner, the upper and lower endplate assemblies are able to pivot about the longitudinal axis to passively account for the mismatch of the oblique angle of insertion and/or the desired sagittal angle.

According to another embodiment, the implant system may include an expandable implant and an inserter instrument. The implant may include an upper endplate assembly including a first upper outer endplate, a second upper outer endplate, and a third upper central endplate positionable between the first and second upper outer endplates. The implant may include a lower endplate assembly including a first lower outer endplate, a second lower outer endplate, and a third lower central endplate positionable between the first and second lower outer endplates. The implant may include an actuator assembly including a rotatable actuator having a shaft and a rotatable nut. The implant may include a plurality of driving ramps including a front ramp, a mid-ramp, and a rear ramp positioned along the shaft of the actuator. The implant may include an upper ramp connected to the upper endplate assembly and engaged with the plurality of driving ramps. The implant may include a lower ramp connected to the lower endplate assembly and engaged with the plurality of driving ramps. The upper and lower endplate assemblies are configured to expand in width when the central endplates slide between the outer endplates, and rotation of the actuator and/or the nut may cause independent movement of one or more of the plurality of driving ramps, thereby causing an expansion in height of the upper and lower endplate assemblies. The inserter instrument may include a cannula configured for deploying the implant into a disc space. The cannula may include a pair of opposed tabs configured to engage the implant to keep the implant from advancing too far into the disc space. The tabs may include t-shaped tabs configured to mate with corresponding slots in the sides of the implant.

According to yet another embodiment, an expandable implant includes a plurality of upper endplates, a plurality of lower endplates, an actuator assembly, a plurality of driving ramps, and upper and lower ramps. The plurality of upper endplates may include a first plurality of links configured to articulate into a generally polygonal shape. The plurality of lower endplates may include a second plurality of links configured to articulate into the generally polygonal shape. The actuator assembly may include a rotatable actuator having a shaft. The plurality of driving ramps may include a front ramp and a rear ramp positioned along the shaft of the actuator. The upper ramp may be connected to the plurality of upper endplates and engaged with the plurality of driving ramps. The lower ramp may be connected to the plurality of lower endplates and engaged with the plurality of driving ramps. The upper and lower endplates may be configured to expand in width. Rotation of the actuator may cause movement of one or more of the driving ramps, which press against the upper and lower ramps, thereby causing an expansion in height of the upper and lower endplates.

The first and second plurality of links may each include a front link and a rear link configured to mate with the upper and lower ramps, respectively. The first and second plurality of links may expand in width when the rear links move towards the front links. The shaft of the actuator may include a threaded portion and a non-threaded portion. The front ramp may be positioned on the non-threaded portion of the actuator, and the rear ramp may be positioned on the threaded portion of the actuator. Rotation of the actuator may cause the rear ramp to move away from the front ramp, which presses the upper and lower ramps away from one another, thereby expanding the upper and lower endplates in height.

The upper and lower endplates may be configured to passively pivot about a longitudinal axis of the implant. For example, the upper and lower ramps may each include a first tab extending outwardly from a proximal end of the ramp and a second tab extending outwardly from a distal end of the respective ramps. The first and second tabs may engage with the endplates, respectively. A portion of the first and second tabs may be rounded about a longitudinal axis of the implant, which thereby facilitates pivotal movement of the endplates about the longitudinal axis of the implant. In this manner, the upper and lower endplates are able to pivot about the longitudinal axis to passively account for the mismatch of the oblique angle of insertion and/or the desired sagittal angle.

According to yet another embodiment, methods of installing the expandable implants are provided. A disc space of a patient may be accessed and prepared from a posterior approach. A collapsed implant may be positioned within the disc space via a cannula from an oblique approach. The implant may be expanded in width to a widened configuration. The implant may be expanded in height to an expanded configuration. The endplates may passively pivot about a longitudinal axis of the implant for optimal positioning. The cannula may be withdrawn from the patient's body, thereby leaving the implant in the expanded position.

Also provided are kits including expandable fusion devices of varying types and sizes, rods, fasteners or anchors, k-wires, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIGS. 1A-1C are lateral, top, and perspective views, respectively, of an expandable fusion device according to one embodiment, in a fully collapsed position, shown with a cannula for positioning the expandable device on a lower vertebra (the upper adjacent vertebra being omitted for clarity);

FIGS. 2A-2C show lateral, top, and perspective views, respectively, of the expandable fusion device of FIGS. 1A-1C positioned on the lower vertebra (the upper adjacent vertebra being omitted for clarity);

FIGS. 3A-3C show lateral, top, and perspective views, respectively, of the expandable fusion device of FIGS. 2A-2C beginning to expand in width;

FIGS. 10A-10D show side, cross-sectional, perspective, and rear views, respectively, of an expandable fusion device according to one embodiment with a cable or wire for installing the device;

FIGS. 18A-18D show lateral, top, rear, and perspective views, respectively, of the expandable fusion device of FIG. 13 implanted in a disc space;

FIGS. 20A-20D show lateral, top, rear, and perspective views, respectively, of the expandable fusion device of FIGS. 19A-19D implanted in a disc space.

DETAILED DESCRIPTION OF THE INVENTION

Figures 4A, 4B, 4C:
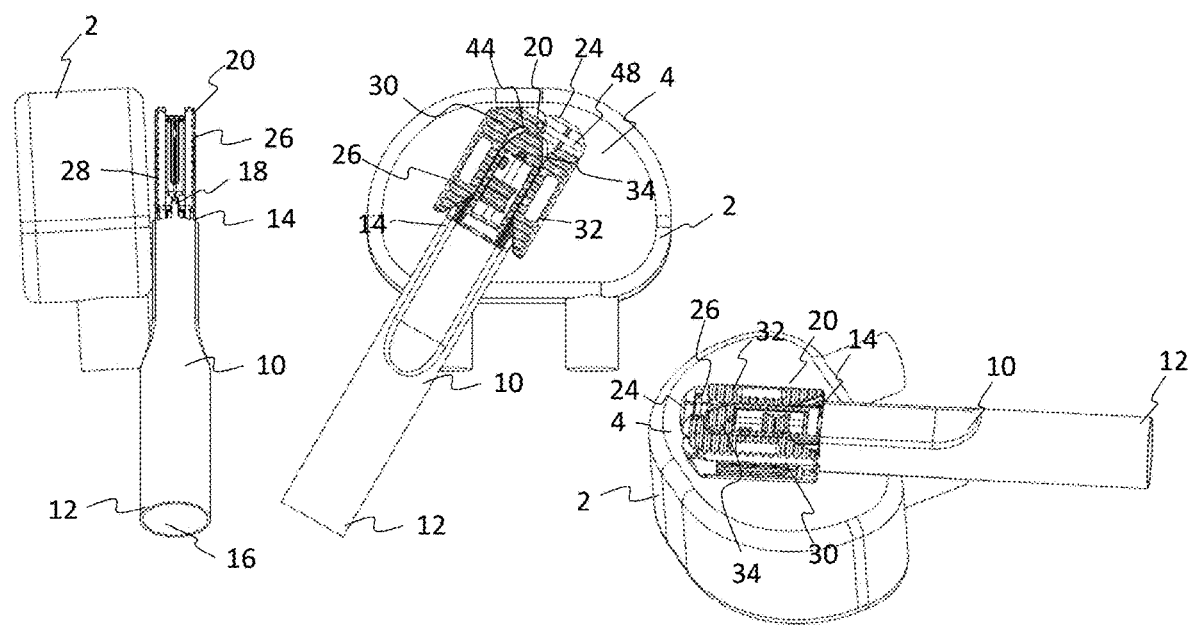
FIGS. 4A-4C show lateral, top, and perspective views, respectively, of the expandable fusion device of FIGS. 3A-3C fully expanded in width.

In order to improve the access profile of the interbody while maximizing cortical bone contact surface area, the interbody implant may be positioned within the disc space with a narrow profile that expands in width to increase surface area contact. The implant may be configured to expand in height to restore anatomical spinal alignment. While expanding in height, the anterior and/or posterior heights of the implant may be individually adjusted, for example, to adjust sagittal balance correction. Accordingly, embodiments of the present application are generally directed to devices, systems, instruments, and methods for installing, and expanding the interbody implant in width and/or height. The terms implant, interbody, interbody implant, fusion device, spacer, and expandable device may be used interchangeably herein.

Referring now to FIGS. 1A-9, an expandable interbody fusion device or implant 20 and method of installation according to one embodiment is shown. The expandable device 20 is configured to expand in both width and height. The implant 20 is configured to be inserted in a collapsed orientation, which defines its smallest dimensions in both width and height. Once inserted into the disc space, the implant 20 is actuated to have an increased width, thereby providing an expanded footprint that fully maximizes surface contact area with the vertebral body 2. The implant 20 is then expanded in height to an expanded orientation to precisely restore normal spinal alignment and evenly distribute the load across the vertebral endplates 4.

The implant 20 extends from a rear end or proximal end 22 configured to connect with an insertion instrument to a nose end or distal end 24 configured to be inserted first into the disc space. The implant 20 includes a plurality of upper endplates 26 and a plurality of lower endplates 28, which are configured to engage with the adjacent vertebrae 2. The plurality of upper endplates 26 may include a first upper outer endplate 30, a second upper outer endplate 32, and a third upper central endplate 34 positionable between the first and second upper outer endplates 30, 32. Similarly, the plurality of lower endplates 28 may include a first lower outer endplate 36, a second lower outer endplate 38, and a third lower central endplate 40 positionable between the first and second lower outer endplates 36, 38. The central endplates 34, 40 are configured to expand the respective outer endplates 30, 32, 36, 38 outwardly, thereby expanding the overall width of the implant 20.

With emphasis on FIGS. 1A-1C, the expandable fusion device or implant 20 is shown with a guide tube or cannula 10 for deployment of the device 20 into a disc space between adjacent vertebral bodies 2 (the upper vertebra is omitted for clarity). The cannula 10 may be suitable for use during a minimally invasive surgical (MIS) procedure, for example. The guide tube or cannula 10 extends from a proximal end 12 to a distal end 14 positionable within the disc space. The cannula 10 defines a central longitudinal opening 16 configured to guide the implant 20 into the disc space. The disc space may be accessed through a posterior approach. The cannula 10 may be docked on the disc space through Kambin's triangle, or the anatomical area that is bordered by the disc space, exiting nerve root, and traversing nerve root. For example, as shown, the cannula 10 may be angled relative to the vertebra 2. For example, the cannula may be angled about 30° relative to a straight posterior access approach.

Turning now to FIGS. 2A-2C, the implant 20 is inserted into the disc space in a fully collapsed orientation, which is collapsed in both width and height, through the cannula 10 to its final position. The widening expansion will be described with reference to the upper endplates 26. It will be appreciated that the lower endplates 28 expand in the same manner. In the collapsed orientation, the outer endplates 30, 32 are nested together. The outer endplates 30, 32 may be positioned in contact or close to one another. As the implant 20 reaches its final position, one or more tabs 18 on the cannula 10 engage the implant 20 to keep it from advancing further into the disc space. The tabs 18 may include a pair of opposed tabs 18, for example, provided on opposite sides of the implant 20. In one embodiment, the tabs 18 include t-shaped tabs configured to mate with corresponding slots in the sides of the implant 20. The t-shaped tab 18 may have a narrow body and an enlarged free end, thereby defining a substantially t-shaped member extending distally from the distal end 14 of the cannula 10. Although t-shaped tabs 18 are exemplified in this embodiment, it will be appreciated that the tabs 18 may be otherwise shaped or configured to engage and retain the implant 20.

Turning now to FIGS. 3A-3C, the implant 20 is beginning to expand in width. The central wedge endplate 34 is configured to move the outer endplates 30, 32 outwardly. As the outer endplates 30, 32 begin to expand away from one another, a gap 42 is formed between the outer endplates 30, 32. The central endplate 34 has a nose portion 44. The nose portion 42 may be angled, tapered, or pointed to facilitate insertion between the outer endplates 30, 32. As the nose portion 44 is moved forward distally and into the gap 42 the outer endplates 30, 32 continue to widen outwardly. The central endplate 34 may be configured to slide between the outer endplates 30, 32 on one or more tracks 46. The track or tracks 46 may include one or more corresponding channels and rails, for example. As the central endplate 34 continues to advance forward distally along the tracks 46, the outer endplates 30, 32 expand in width. The central endplate 34 wedges out the expanding footprint endplates 30, 32. The second outer endplate 32 may include an elongate groove 48 and the first outer endplate 30 may retain a pin 50 configured to be received within the elongate groove 48. As the outer endplates 30, 32 move outwardly, the pin 50 is guided along the path of the groove 48. For example, a linear groove 48 shown in this embodiment provides for a generally parallel expansion in width of the first and second outer endplates 30, 32. It will be appreciated that the groove 48 could be angled, curved, or otherwise configured to provide for the desired type of expansion in width.

With further emphasis on FIGS. 4A-4C, the implant 20 is shown fully expanded in width. The nose 44 of the central endplate 34 moves forward distally, and the central endplate 34 substantially fills the gap 42 between the outer endplates 30, 32. The central endplate 34 is fully advanced to engage the front of the expanding footprint endplates 30, 32. The expanded footprint fully maximizes surface contact area of the endplate 26 with the vertebral body 2. Once in the widened orientation shown, the implant 20 is ready to be expanded in height.

Figure 5A:
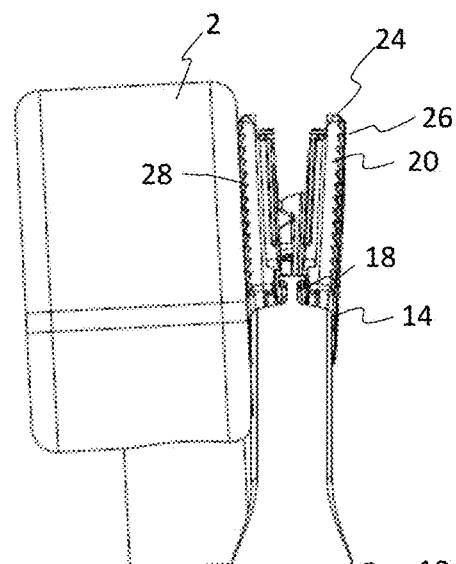
FIGS. 5A-5C show lateral, top, and perspective views, respectively, of the expandable fusion device of FIGS. 4A-4C starting to expand in height.
Figure 5B:
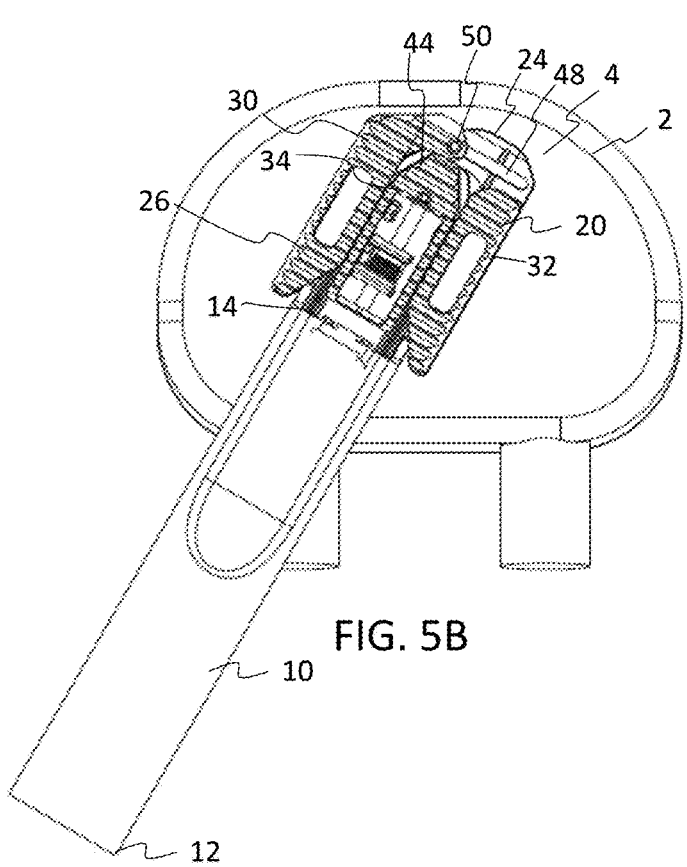
Figure 5C:
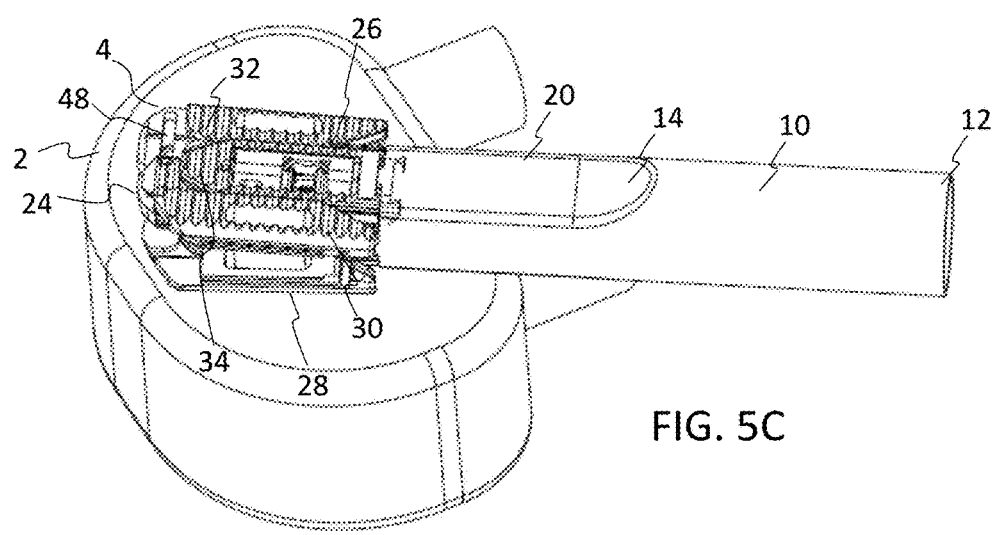
Figure 6A:
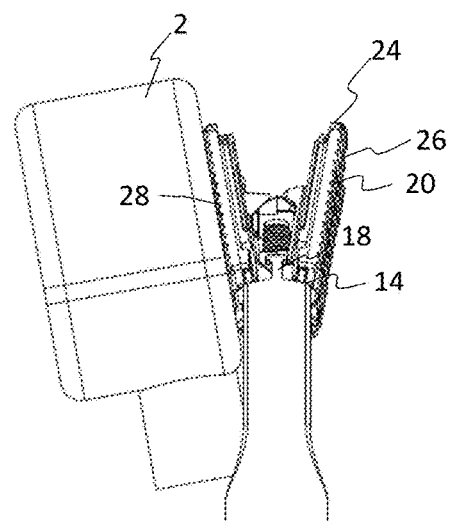
FIGS. 6A-6C show lateral, top, and perspective views, respectively, of the expandable fusion device of FIGS. 5A-5C fully expanded in height.
Figure 6B:
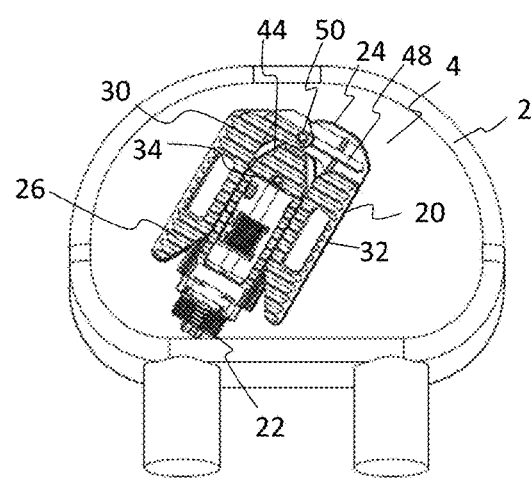
Figure 6C:
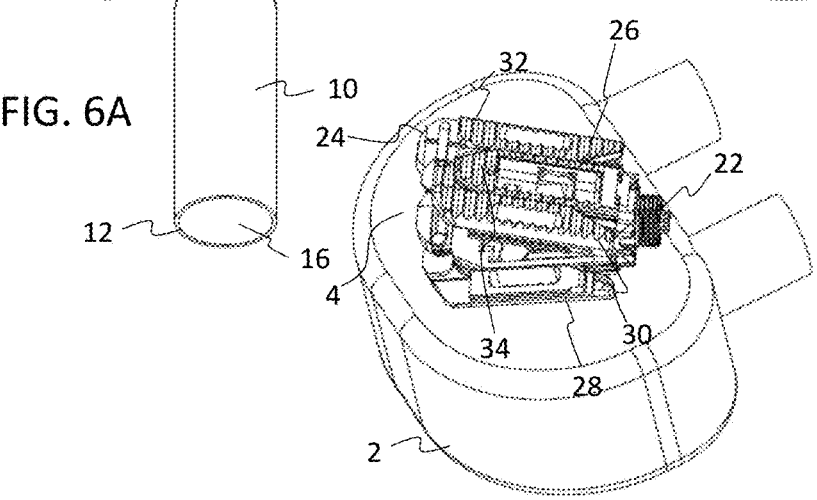

Turning now to FIGS. 5A-5C, the implant 20 is beginning to expand in height. As the implant 20 is expanded, the implant 20 may independently adjust the anterior and/or posterior aspects of the implant 20 to control sagittal balance. When each endplate 26, 28 comes in contact with the vertebral endplates 4, the upper and lower endplates 26, 28 may be configured to passively pivot to maximize the force distribution across the vertebral endplates 4. With further emphasis on FIGS. 6A-6C, the implant 20 is expanded in height and width. The implant 20 may continue to be expanded to adjust correction and sagittal balance and the passive joint may continue to adjust as needed.

Figure 7:
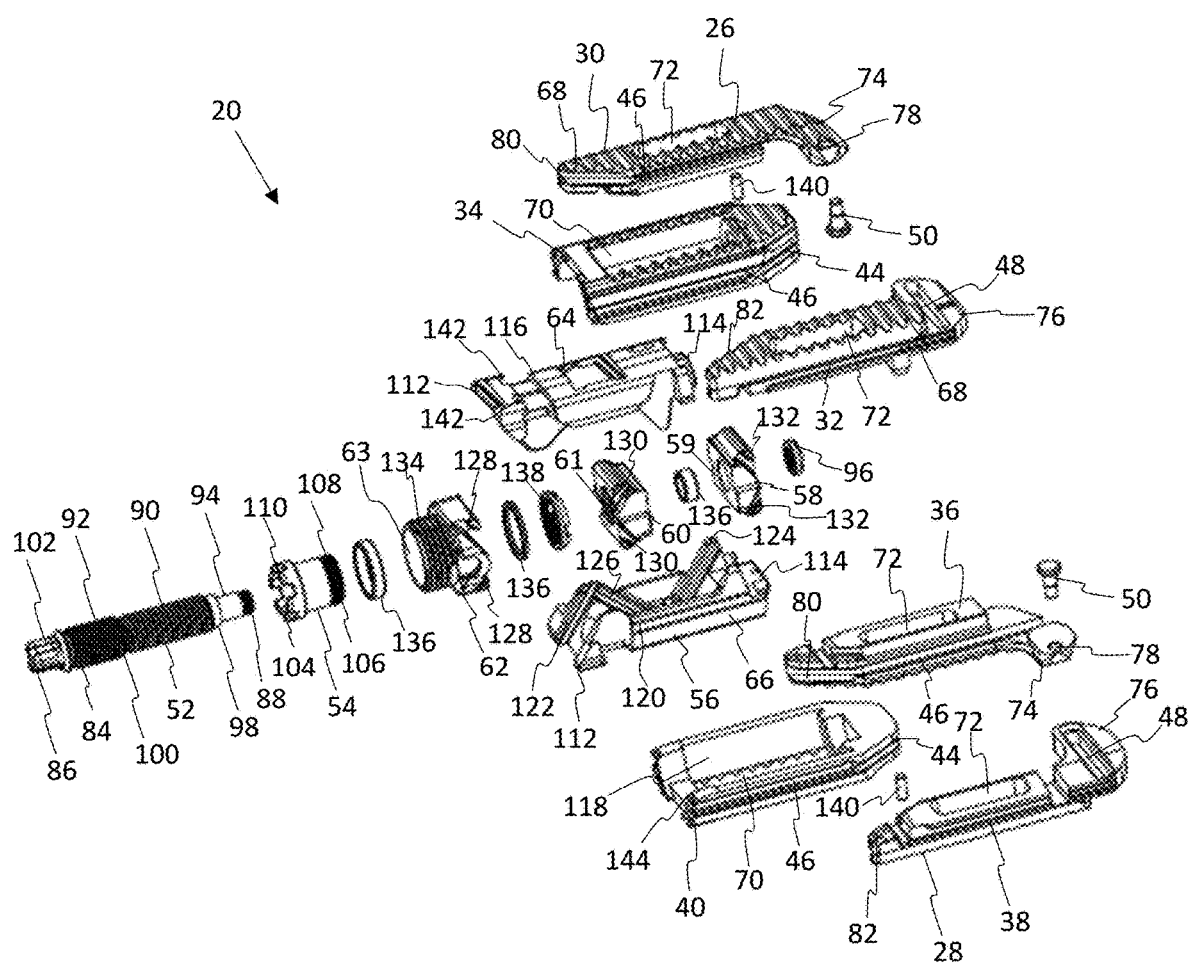
FIG. 7 shows an exploded view of the expandable fusion device of FIGS. 1A-6C.

With emphasis on FIG. 7, an exploded view of the implant 20 is shown. The implant 20 includes a first assembly or first plurality of upper endplates 26 and a second assembly or second plurality of lower endplates 28 configured to engage adjacent vertebrae 2. The implant 20 includes an actuation mechanism including an actuator 52 and a nut 54 configured to move a plurality of internal ramps 56, which expand the endplate assemblies 26, 28 in height. The plurality of ramps 56 may include a plurality of driving ramps including a front ramp 58, a mid-ramp 60, and a rear ramp 62. The front ramp 58 may include a central longitudinal bore 59, the mid-ramp 60 may include a central longitudinal bore 61, and the rear ramp 62 may include a central longitudinal bore 63. The plurality of driving ramps 58, 60, 62 may be positioned along the length of the actuator 52 and are configured to engage and drive an upper ramp 64 and a lower ramp 66, respectively. The upper and lower ramps 64, 66 are connected to the upper and lower endplate assemblies 26, 28. When one or more of the driving ramps 58, 60, 62 are moved and slide against the upper and lower ramps 64, 66, thereby providing for expansion of the implant 20 in height. The expansion may include the ability to individually adjust the anterior and/or posterior heights of the implant 20.

The upper endplate assembly 26 may include first and second upper outer endplates 30, 32 and central wedge endplate 34 slidable between the upper outer endplates 30, 32 to expand the upper outer endplates 30, 32 in width. The lower endplate assembly 28 may include the first and second lower outer endplates 36, 38 and central wedge endplate 40 slidable between the lower outer endplates 36, 38 to expand the lower outer endplates 36, 38 in width. It will be appreciated that the lower endplates 28 are identical to the upper endplates 26 and the description for the upper endplates 26 provided herein applies equally to the lower endplates 28. One or more of the endplates 30, 32, 34 may include a plurality of teeth 68, protrusions, or other friction enhancing surfaces configured to engage bone. The central endplate 34 may include a large central graft retaining opening or window 70 and the outer endplates 30, 32 may include one or more graft openings or windows 72 configured to receive bone graft or other suitable bone growth enhancing material.

The nose end or distal end 24 of the first outer endplate 30 may include a first projection 74 extending inwardly toward the second outer endplate 32. Similarly, the distal end of the second outer endplate 32 may include a second projection 76 extending inwardly toward the first outer endplate 30. The projection 76 may define elongate groove or opening 48 extending generally perpendicular to the longitudinal axis A of the implant 20. The projection 74 may include an opening 78 for receiving a pin 50 therein. The pin 50 is configured to slide along the elongate opening 48, thereby facilitating expansion of the width of the outer endplates 30, 32. It will be appreciated that the locations of the pin 50 and groove 48 may be reversed in the outer endplates 30, 32.

The rear end or proximal end 22 of the first outer endplate 30 may include an angled portion 80 and the proximal end of the second outer endplate 32 may include a second angled portion 82. The angled portions 80, 82 may be configured to receive the nose portion 44 of the central endplate 34 when the implant 20 is in the fully collapsed position. The inner surfaces of the outer endplates 30, 32 define one or more tracks 46 configured to engage corresponding tracks 46 positioned along the sides of the central endplate 34. The tracks 46 along the nose 44 of the central endplate 34 mate with the corresponding tracks 46 along the angled portions 80, 82 of the outer endplates 30, 32, respectively. As the central endplate 34 is advanced forward to expand the width, the tracks 46 along the edges of the central endplate 34 mate with the corresponding tracks 46 along the inner surfaces of the outer endplates 30, 32. The tracks 46 may include male and female grooves and projections configured to mate with a slidable interface. For example, the tracks 46 may include one or more female channels and one or more male rails enabling the central endplate 34 to slide between the outer endplates 30, 32 and extend them outwardly to widen the footprint of the implant 20.

The implant 20 includes an actuation assembly configured to expand the height of the implant 20. The actuation assembly includes a rotatable actuator 52 and rotatable nut 54 configured to move a plurality of internal ramps 56. The implant 20 includes at least three driving ramps, front ramp 58, mid-ramp 60, and rear ramp 62, which interface with the actuator 52. The actuator 52 may include a shaft 84 extending from a proximal end 86 to a distal end 88. The shaft 84 includes a first threaded portion 90, a second threaded portion 92, and a non-threaded portion 94. The first and second threaded portions 90, 92 may have different attributes including outer diameters, handedness, thread form, thread angle, lead, pitch, etc.

Figure 8A:
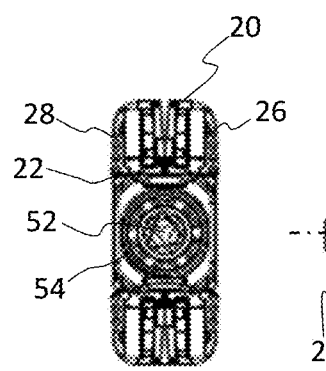
FIGS. 8A-8C are rear, top, and cross-sectional views, respectively, of the expandable fusion device of FIGS. 4A-4C expanded in width and collapsed in height.
Figure 8B:
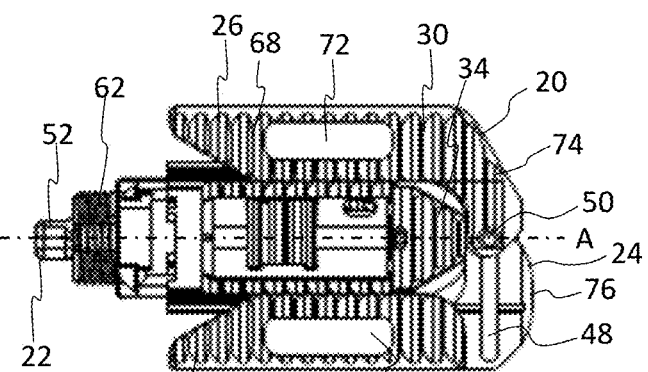
Figure 8C:
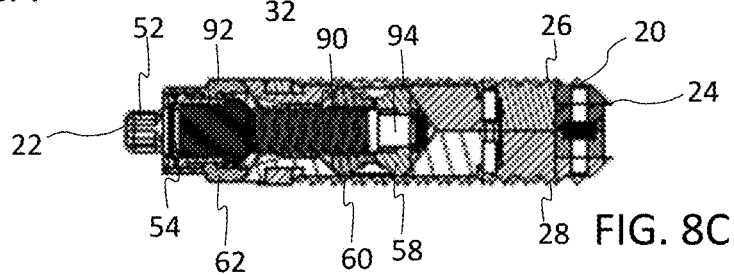
Figure 9A:
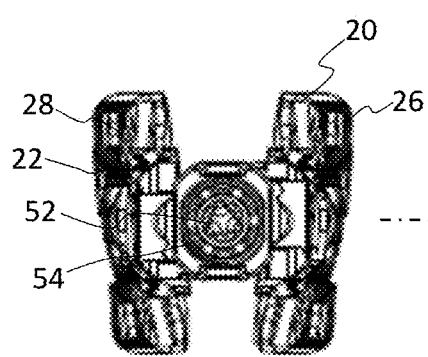
FIGS. 9A-9C are rear, top, and cross-sectional views, respectively, of the expandable fusion device of FIGS. 6A-6C expanded in width and expanded in height.
Figure 9B:
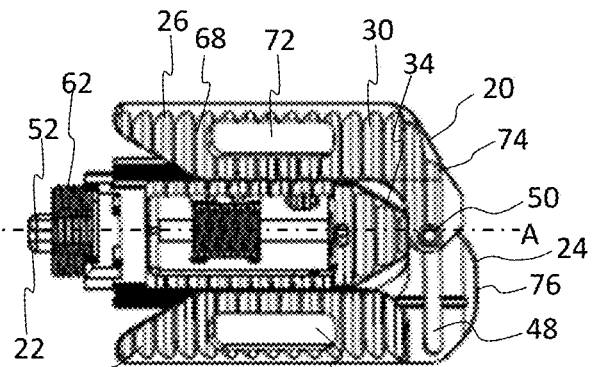
Figure 9C:
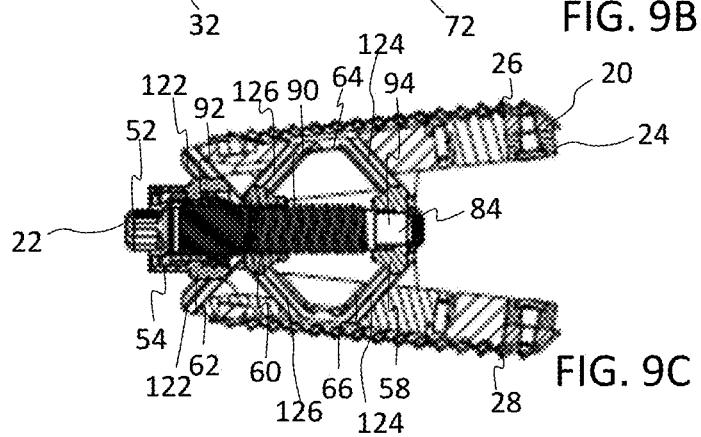

In FIGS. 8A-8C, the implant 20 is shown in a widened orientation and collapsed in height and in FIGS. 9A-9C, the implant 20 is shown in a widened orientation and expanded in height. As best seen in FIG. 9C, the front driving ramp 58 is positioned on the non-threaded portion 94 of the actuator 52. The front driving ramp 58 may be located between a securing washer 96 and a shoulder 98 defined between the first threaded portion 90 and the non-threaded portion 94. In this manner, the front ramp 58 is secured to the actuator shaft 84. In an alternative embodiment, the front ramp 58 may be positioned along another threaded portion in order to move the front ramp 58 along the actuator shaft 84. The mid-ramp 60 is positioned on the first threaded portion 90 and is moveable along the length of the first threaded portion 90 in order to move the mid-ramp 60 and thereby move the upper and lower ramps 64, 66 to expand the implant 20. The rear ramp 62 is positioned along the second threaded portion 92 in order to move the rear ramp 62. The rear ramp 62 is moveable along the length of the second threaded portion 92 to move the upper and lower ramps 64, 66 and expand the implant 20. The first threaded portion 90 may have a smaller outer diameter and different handedness than the second threaded portion 92. The first threaded portion 90 may transition to the second threaded portion 92 at a second shoulder 100. The proximal end 86 of the actuator shaft 84 may include a first instrument retention feature, such as a ribbed neck 102. The ribbed neck 102 may include knurled neck grips or other suitable engagement surfaces, which are configured to interface with a driver instrument to thereby rotate the actuator shaft 84.

The actuation assembly may also include a rotatable nut 54. The rotatable nut 54 may be configured to move the rear ramp 62 independent of the mid-ramp 60 and front ramp 58. The nut 54 may extend from a proximal end 104 to a distal end 106. The distal end 106 may include an outer threaded portion 108 configured to mate with a corresponding internal threaded portion in the bore 63 through the rear driving ramp 62. The proximal end 104 may include a second instrument retention feature, such as a slotted head 110. The slotted head 110 may include slots or other suitable engagement surfaces configured to interface with a driver instrument to thereby rotate the nut 54. When only the nut 54 is rotated clockwise, the rear ramp 62 is translated forward, decreasing it's distance to the front ramp 58 and the posterior height increases and the anterior height decreases thus decreasing the lordotic angle of the spacer. When the nut 54 remains stationary and only the actuator 52 is rotated clockwise, the mid ramp 60 moves away from the front ramp 58 increasing the anterior height, at the same time the rear ramp 62 moves away relative to the front ramp 58 as the actuator 52 advances through the nut 54. Increasing the gap between the rear ramp 62 and the front ramp 58 increases the lordotic angle of the spacer. When both the actuator 52 and the nut 54 are rotated clockwise at the same time, the rear ramp 62 and the front ramp 58 do not move relative to each other. Only the mid ramp 60 translates away from the front ramp 58 and towards the rear ramp 62. This results in parallel expansion of the endplates 26, 28. It will be appreciated that the movement of the driving ramps 58, 60, 62 and resulting expansion may be operated by the actuator 52 and/or nut 54 with any suitable configurations and mechanisms.

The driving ramps 58, 60, 62 engage with upper ramp 64 and lower ramp 66 to thereby move the upper and lower ramps 64 outwardly in height. It will be appreciated that the lower ramp 66 is identical to the upper ramp 64 and the description for the upper ramp 64 herein applies equally to the lower ramp 66. The upper ramp 64 extends from a proximal end 112 to a distal end 114. The upper ramp 64 includes an outer surface 116 configured to be received within a cavity 118 in the central ramp 34. A portion of the outer surface 116 may be rounded about the longitudinal axis A of the implant 20 to facilitate movement of the endplates 26 about the longitudinal axis A of the implant 20. The outer surface 116 of the upper ramp 64 may define one or more recesses or slots 142 configured to guide one or more corresponding tabs 144 on the inner cavity 118 of the central endplate 34. The slot 142 may include a circular t-slot configured to guide or pivot the central endplate 34 about the longitudinal axis A of the implant 20. In this manner, the upper endplate assembly 26 is configured to passively pivot about the longitudinal axis A to account for lordosis and/or the oblique delivery angle of insertion. Without this type of polyaxial joint, the endplates 26, 28 could dig into and/or tip the vertebral bodies 2 when implanted.

The upper ramp 64 includes an inner surface 120 configured to mate with the driving ramps 58, 60, 62. The inner surface 120 may include one or more ramped surfaces 122, 124, 126. In the embodiment shown, the inner surface 120 includes a first ramped surface 122 near the proximal end 112 of the ramp 64, a second ramped surface 124 near the distal end 114 of the ramp 64, and a third ramped surface 126 between the first and second ramped surfaces 122, 124. The first ramped surface 122 may face the proximal end 112, the second ramped surface 124 may face the proximal end 112, and the third ramped surface 124 may face the distal end 114. The ramped surfaces 122, 124, 126 may be angled continuous surfaces with a given angle of slope. It is contemplated that the slope of the ramped surfaces 122, 124, 126 may be equal or can differ from each other. The ramped surfaces 122, 124, 126 may be generally straight ramped surfaces or may be curved ramped surfaces. The ramped surfaces 122, 124, 126 may include male slide ramps or protruding ramps. The first and second ramped surfaces 122, 124 may be spaced apart at an equal distance such that the ramped surfaces 122, 124 are substantially parallel to one another. The third ramped surface 126 may be angled opposite to the first and second ramped surfaces 122, 124. In this way the apex of the third ramp 126 may meet or near the apex of the first ramp 122 and the base of the third ramp 126 may meet or near the base of the second ramp 124. Although a specific arrangement of ramped surfaces 122, 124, 126 is shown, it is envisioned that the number, location, and configuration of ramped surfaces 122, 124, 126 may be modified or selected by one skilled in the art.

The driving ramps 58, 60, 62 may include one or more ramped surfaces 128, 130, 132. The ramped surfaces 128, 130, 132 of the driving ramps 58, 60, 62 may be configured and dimensioned to engage the corresponding ramped surfaces 122, 124, 126 of the upper and lower ramps 64, 66, respectively. For example, the rear ramp 62 may include one or more ramped surfaces 128, mid-ramp 60 may include one or more ramped surfaces 130, and front ramp 58 may include one or more ramped surfaces 132. The ramped surfaces 128, 130, 132 may be angled continuous surfaces with a given angle of slope. It is contemplated that the slope of the ramped surfaces 128, 130, 132 may be equal or can differ from each other. The ramped surfaces 128, 130, 132 may be generally straight ramped surfaces or may be curved ramped surfaces. The ramped surfaces 128, 130, 132 may include female slide ramps or recessed ramps configured to receive the male ramped surfaces 122, 124, 126 of the upper ramp 34. It will be appreciated that the male and female ramps may be reversed or may be otherwise configured to provide for slidable mating between the ramps. The first ramped surface 122 of the upper ramp 34 may be configured to slidably interface with the ramped surface 128 of the driving rear ramp 62. The second ramped surface 124 of the upper ramp 34 may be configured to slidably interface with the ramped surface 132 of the driving front ramp 58. The third ramped surface 126 of the upper ramp 34 may be configured to slidably interface with the ramped surface 130 of the driving mid-ramp 60. As one or more of the driving ramp 58, 60, 62 moves, the ramped surface or surfaces 128, 130, 132 pushes against the corresponding ramped surface or surfaces 122, 124, 126 of the upper and lower ramps 64, 66. In this manner, the individual driving ramps 128, 130, 132 control the rate of expansion of the upper and lower ramps 64, 66, which thereby controls the expansion of the attached upper and lower endplates 26, 28. The upper and lower endplate assemblies 26, 28 are pushed outwardly into the expanded configuration.

The implant 20 may further include one or more of the following features. The driving rear ramp 62 may include an outer threaded portion 134 at the proximal end which may be configured to be retained by an insertion instrument. One or more friction rings or washers 136 may be provided to provide drag or thrust resistance to the nut 54 and/or driving ramps 58, 60, 62, respectively. A locking member 138 may be provided to capture and secure the nut 54 in the assembly. One or more pins 140 may be provided to limit travel and keep the endplates 26 connected together.

In order to improve the access profile of the interbody implant 20 while maximizing cortical bone contact surface area, methods and systems of installing, widening, and/or expanding the implant 20 may include one or more of the following. The implant 20 may enter the disc space with a narrow profile and articulate to increase surface area contact on the anterior apophyseal ring. The orientation and position of the interbody implant 20 in its final implanted position may be optimized by pre-/intra-op scans and/or normal population statistics that determine bone mineral density maps of the vertebral body. Robotic and/or navigation guidance may be used to correctly orient the interbody 20. Further details of robotic and/or navigational systems can be found in U.S. Patent Publication No. 2017/0239007, which is incorporated herein by reference in its entirety for all purposes.

In one embodiment, the implant 20 may be implanted with one or more of the following steps: (1) A determination is made on final optimal implant location to optimize bone mineral density of the contacted bone/implant interface. (2) Robotic and/or navigation is used to determine the potential trajectories that will allow for this optimal implant location to be achieved. (3) The cannula 10 is docked on the disc space through Kambin's triangle, or the anatomical area that is bordered by the disc space, exiting nerve root, and traversing nerve root. (4) The expandable interbody 20 is inserted in the non-articulated, non-expanded orientation. (5) The expandable interbody 20 is actuated into the expanded or widened footprint that fully maximizes surface contact area with the vertebral body. (6) The expandable interbody 20 is then expanded in height to precisely restore normal spinal alignment and evenly distribute the load across the vertebral endplates 4.

Turning now to FIGS. 10A-10D, an expandable interbody fusion device or implant 150 according to another embodiment is shown. Implant 150 expands in width similar to implant 20 with a central wedge endplate 164. In this embodiment, the cannula 10 is replaced with one or more cables or wires 196, which is connected to each endplate to hold them in position while advancing the central wedge endplate 164 forward to widen the footprint of the implant 150. The cable or wire 196 may be looped through the endplate assemblies 156, 158 and out to the back of the instrumentation for holding.

The implant 150 extends from a rear end or proximal end 152 configured to connect with an insertion instrument to a nose end or distal end 154 configured to be inserted first into the disc space. The implant 150 includes a first assembly or first plurality of upper endplates 156 and a second assembly or second plurality of lower endplates 158 configured to engage adjacent vertebrae 2. The upper endplate assembly 156 may include first and second upper outer endplates 160, 162 and the lower endplate assembly 158 may include first and second lower outer endplates 166, 168. The central wedge endplate 164 is slidable between the outer endplates 160, 162, 166, 168 to thereby expand the outer endplates 160, 162, 166, 168 in width. The central endplate 164 may include one or more graft retaining openings or windows 170 configured to receive bone graft or other suitable bone growth enhancing material.

The distal end 154 of the implant 150 may include a nose assembly 172 including an upper nose portion 174, a lower nose portion 176, and a central nose portion 178 positioned between the upper and lower nose portions 174, 176. The upper and lower endplates 156, 158 connect to the nose assembly 172 with one or more pivotable linking members or links 180. The distal end of the first upper endplate 160 connects to one of end of a first linking member 180 with a first pivot pin 182 and the opposite end of the linking member 180 connects to the upper nose 174 with a second pivot pin 182. Similarly, the distal end of the second upper endplate 162 connects to one of end of a second linking member 180 with a third pivot pin 182 and the opposite end of the linking member 180 connects to the upper nose 174 with a fourth pivot pin 182. The lower endplates 158 are connected to the lower nose portion 176 with additional links 180 and pivot pins 182 in the same manner.

The proximal ends of the outer endplates 156, 158 may each include an angled portion 184 configured to receive the nose portion 186 of the central endplate 164 when the implant 150 is in the fully collapsed position. The inner surfaces of the outer endplates 156, 158 may define one or more tracks 188 configured to engage corresponding tracks 188 positioned along the sides of the central endplate 164. The tracks 188 along the nose 186 of the central endplate 164 mate with the corresponding tracks 188 along the angled portions 184 of the outer endplates 156, 158, respectively. As the central endplate 164 is advanced forward to expand the width, the tracks 188 along the edges of the central endplate 164 mate with the corresponding tracks 188 along the inner surfaces of the outer endplates 160, 162. The tracks 188 may include male and female grooves and projections configured to mate with a slidable interface. For example, the tracks 188 may include one or more female channels and one or more corresponding male rails enabling the central endplate 164 to slide between the outer endplates 156, 158 and extend them outwardly to widen the footprint of the implant 150. One or more of the tracks 188 may form a slidable dovetail configuration.

The proximal end 152 of the implant 150 includes a rear assembly 190 for securing one or more cables or wires 196. The rear assembly 190 may include a ring 192 and a base 194 positioned between the ring 192 and the slidable central endplate 164. The rear assembly 190 may be configured for attachment to an insertion instrument, for example. The cable or wire 196 may be looped through the endplate assemblies 156, 158 and out to the back of the instrumentation for holding. The wire 196 may be secured to the ring 192 at the proximal end 152 of the implant 150 and loop around the implant 150. For example, as best seen in FIG. 10B, the wire 196 may connect to the ring 192 at a first location, extend along a first side of the central wedge endplate 164, bend inwardly following the nose 186 of the central wedge endplate 164, travel along an inner surface of the outer endplates 156, 158, pinch inwardly near the links 180, loop around the central nose 178 of the nose assembly 172, pinch inwardly near the links 180, travel along an inner surface of the outer endplates 156, 158, bend outwardly following the nose 186 of the central wedge endplate 164, extend along a second side of the central wedge endplate 164 and reconnect to the ring 192 at a second location opposite to the first location. The wire 196 may be recessed into a central male track 188 extending along the side of the central wedge endplate 164. The cable or wire 196 may be configured for holding the implant 150 during the widening expansion.

Figure 11A:
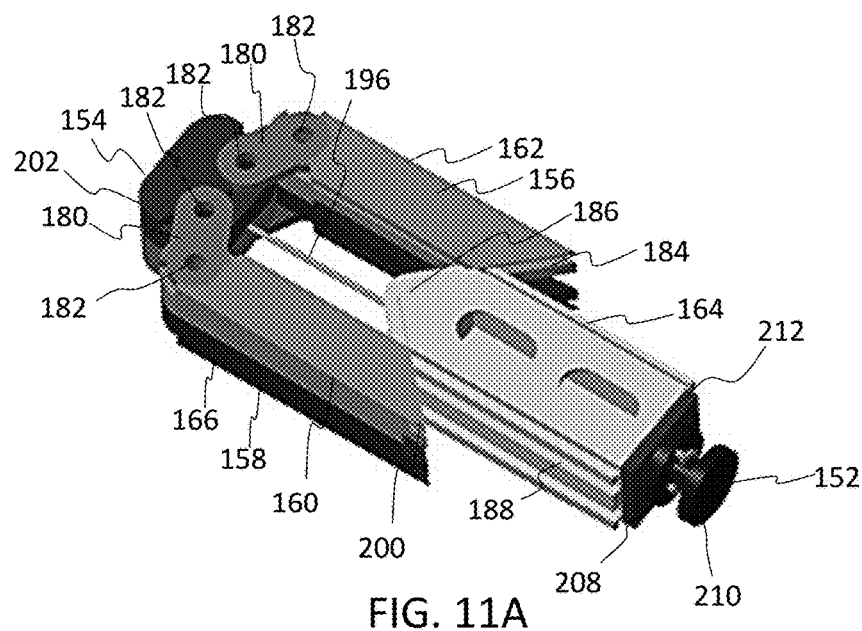
FIGS. 11A-11B show perspective and cross-sectional views, respectively, of an expandable fusion device with a cable or wire according to another embodiment.
Figure 11B:
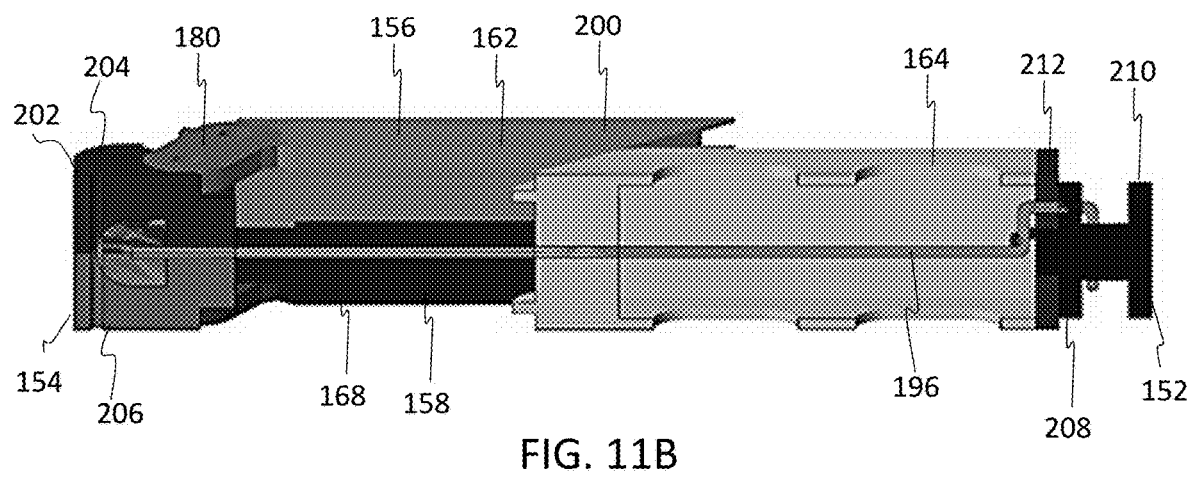

Turning now to FIGS. 11A-11B, an expandable interbody fusion device or implant 200 according to another embodiment is shown. Implant 200 is similar to implant 150 except the cable or wire 196 extends centrally through the implant 200. The wire 196 may connect to the nose assembly 202 to hold each of the outer endplates 156, 158 in position while advancing the central endplate 164 forward. The wire 196 may connect to the back of the instrumentation for holding. In this embodiment, the nose assembly 202 includes an upper nose 204 connected to a lower nose 206 and the rear assembly 208 includes a pin 210 and a base 212. A first end of the cable or wire 196 anchors into the upper and lower nose portions 204, 206 at the distal end 154 and the second end of the wire 196 attaches to the pin 210 at the proximal end 152. The wire 196 may extend along the central longitudinal axis of the implant 200 from the nose assembly 202, through the central wedge endplate 164, through the base 212, and transversely into the pin 210. The central wedge endplate 164 may slide along the wire 196 and as the central endplate 164 moves forward, the central endplate 164 expands the outer endplates 156, 158 in the same manner as described herein for implant 150.

Figure 12A:
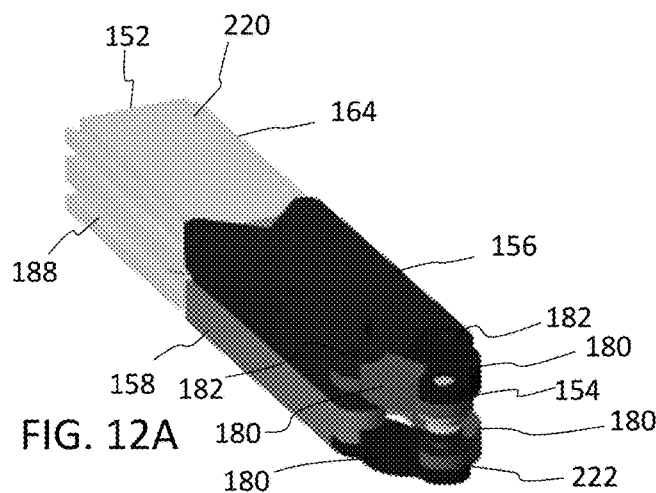
FIGS. 12A-12C show front perspective views collapsed and expanded in width and a top view, respectively, of an expandable fusion device according to yet another embodiment.
Figure 12B:
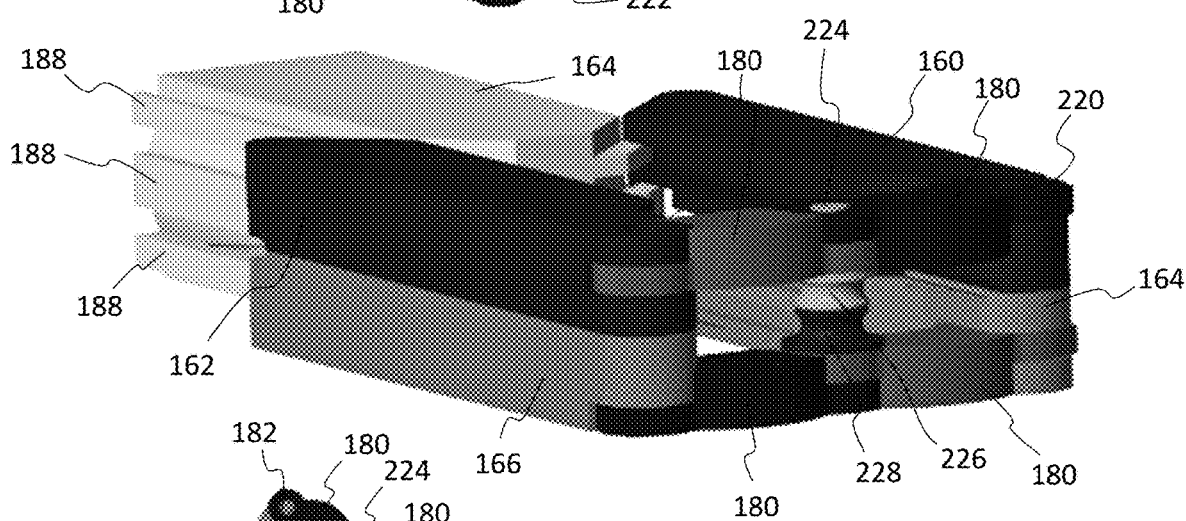
Figure 12C:
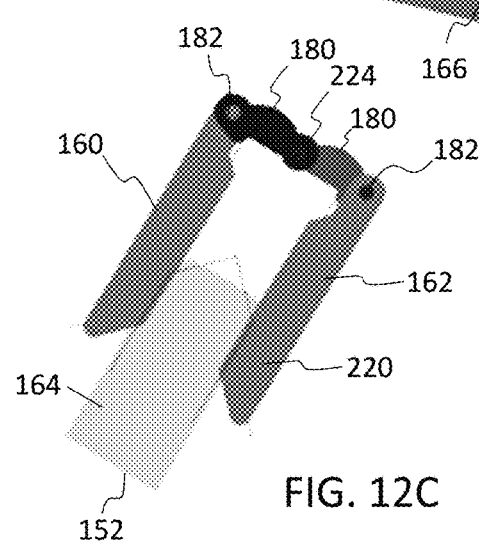

Turning now to FIGS. 12A-12C, an expandable interbody fusion device or implant 220 according to another embodiment is shown. Implant 220 is similar to implants 150, 200 except the nose is replaced with a pin assembly 222. The pin assembly 222 may include one or more elongate pins 224, a first collar 226 surrounding and rotatable about the pin 224, and a second collar 228 surrounding and rotatable about the pin 224. The elongate pin 224 may extend from an upper surface of the upper endplates 156 to a lower surface of the lower endplates 158. The first collar 226 may connect to the upper links 180 rotatably coupled to the upper endplates 156 and the second collar 228 may connect to the lower links 180 rotatably coupled to the lower endplates 158. In the collapsed position shown in FIG. 12A, the links 180 pivot inwardly, thereby allowing the outer endplates 156, 158 to contact or be positioned near one another to provide a minimum width for the implant 200. As the central wedge endplate 164 is advanced forward toward the distal end 154, the tracks 188 of the central wedge endplate 164 slide along the mating tracks 188 along the inner surfaces of the outer endplates 160, 162, 164, 168. In this embodiment, the tracks 188 along the central wedge endplate 164 include a male upper track 188, a lower male track 188, and a central male track 188 positioned between the upper and lower male tracks 188. The male tracks 188 are separated by elongate grooves. The pin assembly 222 and the pin 182 connecting the links 180 to the respective endplates 160, 162, 164, 168 allow the endplates 160, 162, 164, 168 to expand in width when the central endplate 164 slides along the mating tracks 188. As the links 180 pivot outwardly, the outer endplates 156, 158 move away from one another to provide a maximum width for the implant 200.

Referring now to FIGS. 13-18D, an expandable interbody fusion device or implant 230 and method of installation according to one embodiment is shown. The expandable device 230 is configured to expand in both width and height. The implant 230 is configured to be inserted in a collapsed orientation, which defines its smallest dimensions in both width and height. Once inserted into the disc space, the implant 230 is actuated to have an increased width, thereby providing an expanded footprint that fully maximizes surface contact area with the vertebral body 2. The implant 230 is then expanded in height to an expanded orientation to precisely restore normal spinal alignment and evenly distribute the load across the vertebral endplates 4.

Figure 13:
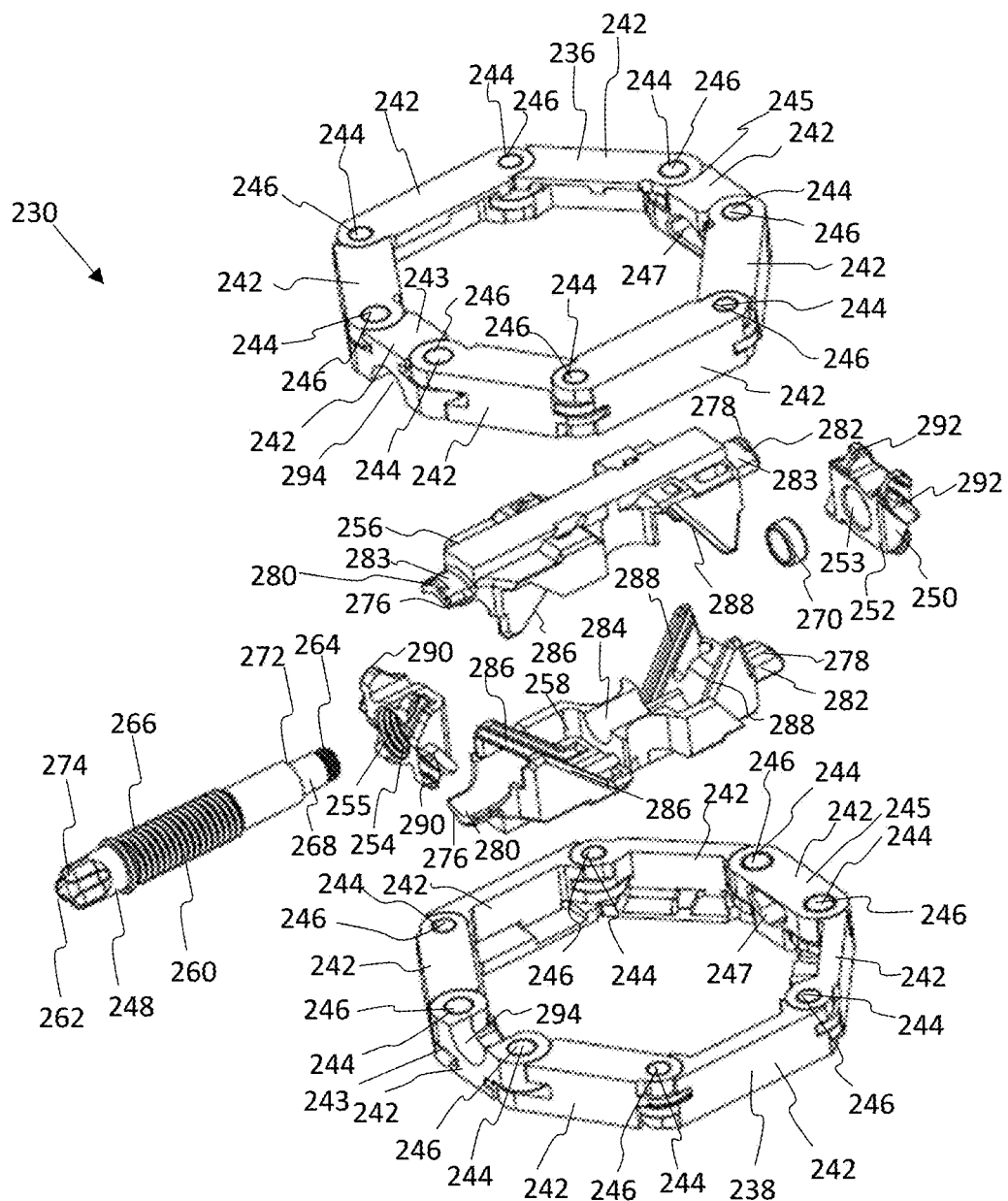
FIG. 13 is an exploded view of an expandable fusion device with a plurality of links according to another embodiment.
Figure 14A:
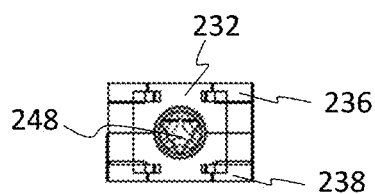
FIGS. 14A-14E show rear, perspective, top, side, and front views, respectively, of the expandable fusion device of FIG. 13 in a fully collapsed position.
Figure 14B:
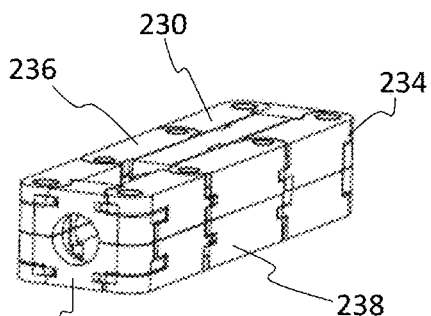
Figure 14C:
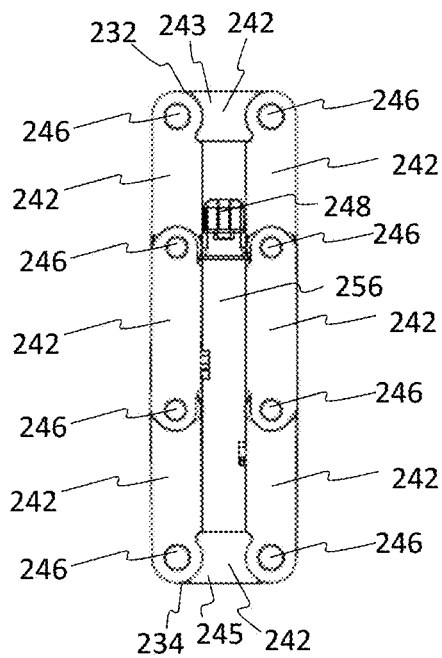
Figure 14D:
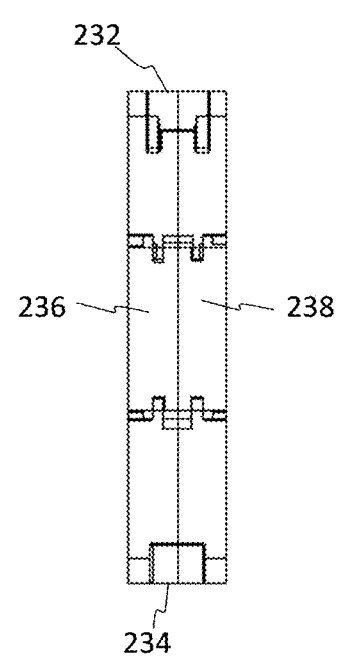
Figure 14E:
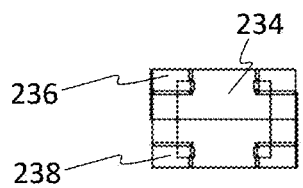
Figure 15A:
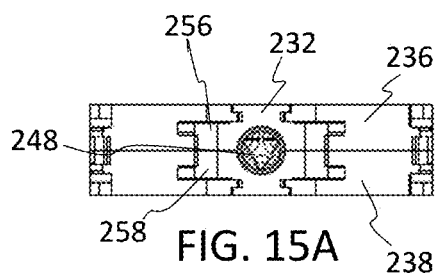
FIGS. 15A-15E show rear, perspective, top, side, and front views, respectively, of the expandable fusion device of FIGS. 14A-14E expanded in width and collapsed in height.
Figure 15B:
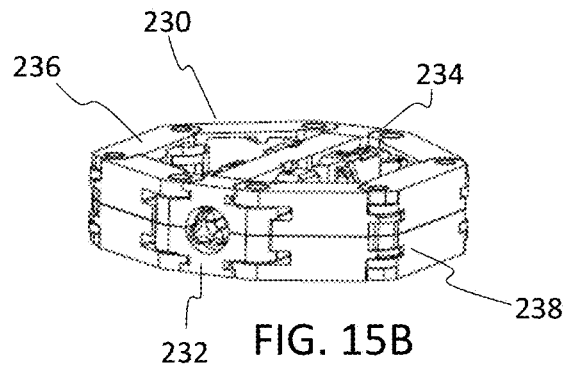
Figure 15C:
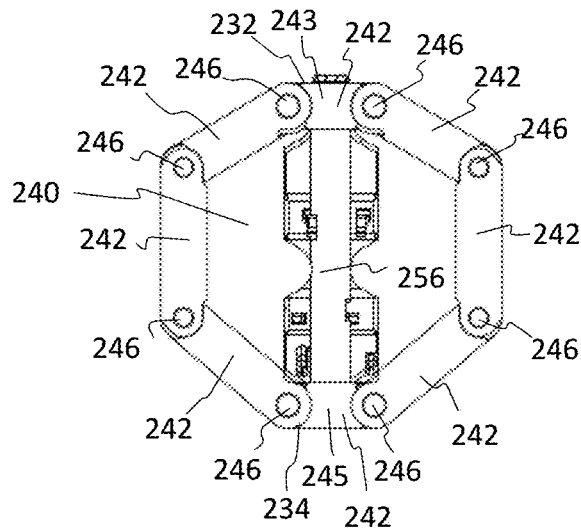
Figure 15D:
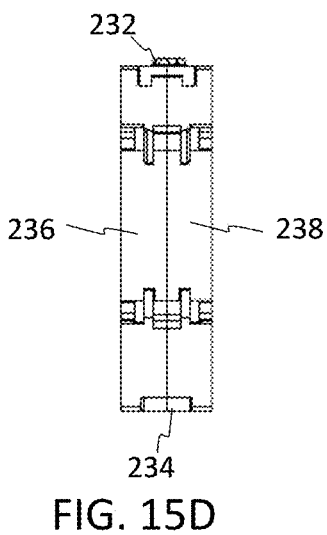
Figure 15E:
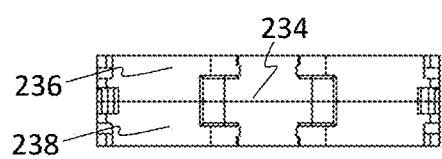
Figure 16A:
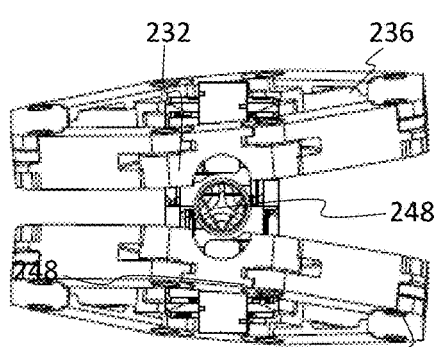
FIGS. 16A-16E show rear, perspective, top, side, and front views, respectively, of the expandable fusion device of FIGS. 15A-15E expanded in width and expanded in height.
Figure 16B:
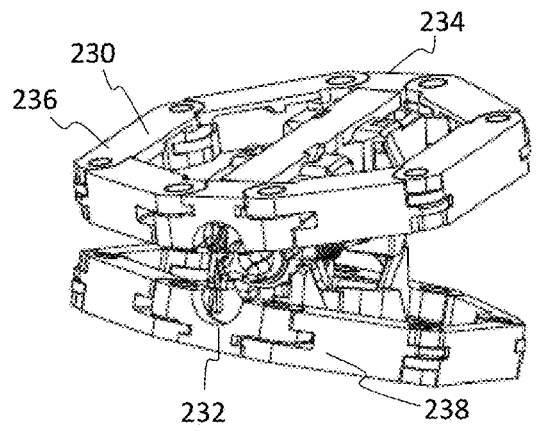
Figure 16C:
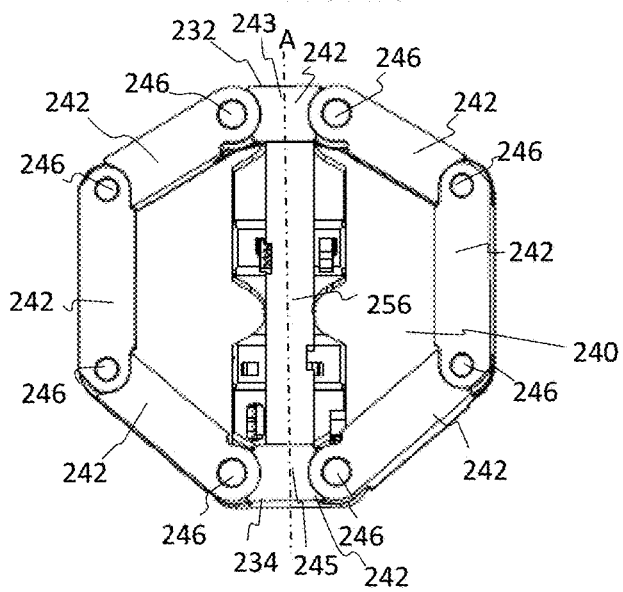
Figure 16D:
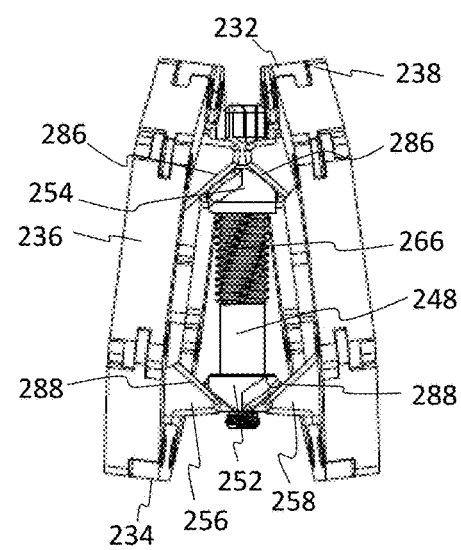
Figure 16E:
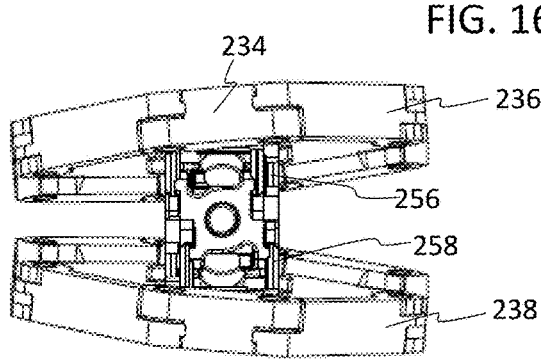

In FIG. 13, an exploded view of the implant 230 is shown. FIGS. 14A-14E show the implant 230 in the collapsed configuration, minimized in both width and height. FIGS. 15A-15E show the implant 230 in a widened configuration with the implant 230 increased in width. FIGS. 16A-16E show the implant 230 in an expanded configuration with the implant 230 increased in width and height. The implant 230 extends from a rear end or proximal end 232 configured to connect with an insertion instrument to a nose end or distal end 234 configured to be inserted first into the disc space. The implant 230 includes a first assembly or first plurality of upper endplates 236 and second assembly or second plurality of lower endplates 238, which are configured to engage with the adjacent vertebrae 2. When articulated to the widened footprint, the implant 230 may define one or more central windows or openings 240 extending between the upper and lower endplates 236, 238. The central window or opening 240 may be configured to receive bone graft or a bone growth inducing material. The bone graft can be introduced within and/or around the fusion device 230 to further promote and facilitate the intervertebral fusion.

The upper and lower endplates 236, 238 may each include a plurality of individual linking segments or links 242. It will be appreciated that the lower endplate assembly 238 is identical to the upper endplate assembly 236 and the description for the upper endplates 236 provided herein applies equally to the lower endplates 238. The plurality of linking segments or links 242 may be configured to articulate into a generally polygonal shape. The polygon may be convex, concave, simple, intersecting, or of other suitable type. The shape of the polygon may be dictated by the number of segments or links 242 used to build the implant 230. For example, a device 230 with eight links 20, as shown in this embodiment, may form an octagon. Although the device 230 is shown with eight links 242 for each of the upper and lower endplates 236, 238 forming a generally octagonal shape, it is envisioned that the device 230 may have as few links 242 or as many as desired. The links 242 may have the same length or the links 242 may be of different lengths. In the embodiment shown, the rear-most link 243 and front-most link 245 have a shorter length than the remaining side links 242, and each of the side links 242 have the same length. It will be appreciated that the links 242 may be of any suitable length.

Each of the links 242 are connected and able to articulate about a pivot joint 244. The pivot joint 244 may be a revolute joint such as a pin joint or hinge joint. For example, the pivot joint 244 may provide a uni-axial rotation or single-axis rotation about one or more pins 246, for example. The connected links 242 may be able to rotate freely about the axis of each respective pin 246 between connected links 242. Although pins 246 are exemplified herein, it will be appreciated that other joint geometries may be used. The implant 230 is inserted in its collapsed position shown in FIGS. 14A-14E. Once inserted, the implant 230 is widened by applying a force to the rear-most link 243, thereby moving the rear-most link 243 forward toward the front-most link 245. As the rear-most link 243 moves forward toward the distal end 234, the links 242 along the sides of the implant 230 pivot outwardly into the widened configuration shown in FIGS. 15A-15E.

The implant 230 includes an actuator assembly including an actuator 248 configured to move a plurality of internal ramps 250, which expand the endplate assemblies 236, 238 in height. The plurality of ramps 250 may include a front driving ramp 252 and a rear driving ramp 254. The front driving ramp 252 may include a central longitudinal bore 253 and the rear driving ramp 254 may include a central longitudinal bore 255. The plurality of driving ramps 252, 254 may be positioned along the length of the actuator 248 and are configured to engage and drive an upper ramp 256 and a lower ramp 258, respectively. The upper and lower ramps 256, 258 are engaged with the upper and lower endplate assemblies 26, 28, thereby providing for expansion of the implant 230 in height.

Figure 17A:
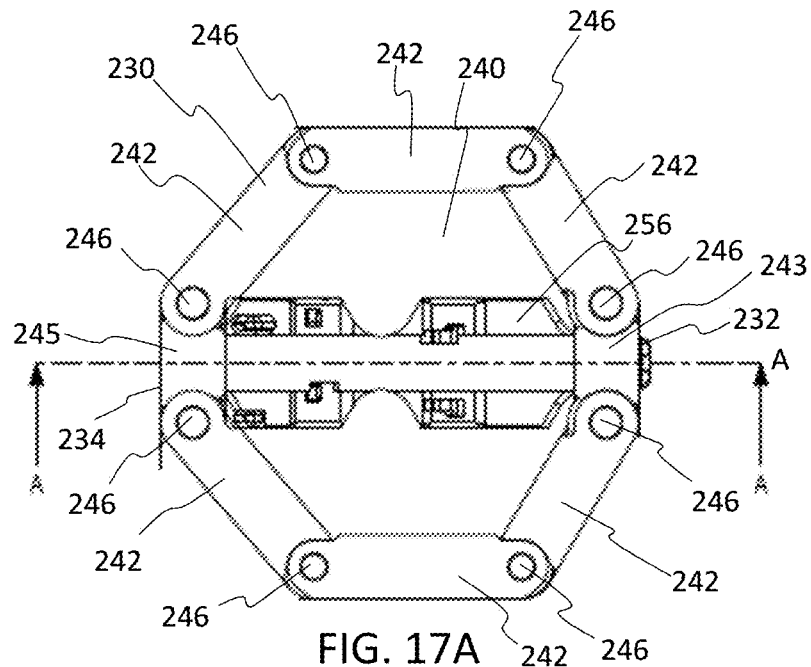
FIGS. 17A-17C show top and cross-sectional views in collapsed and expanded configurations, respectively, of the expandable fusion device of FIG. 13.
Figure 17B:
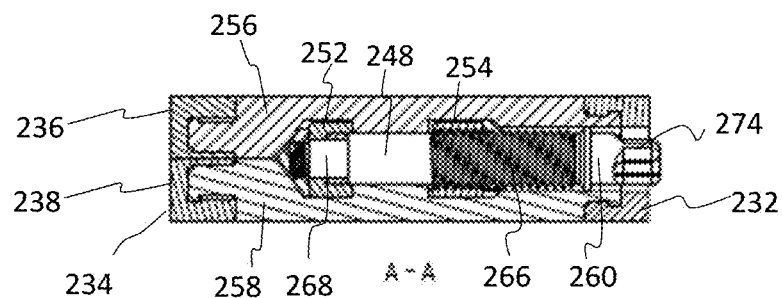
Figure 17C:
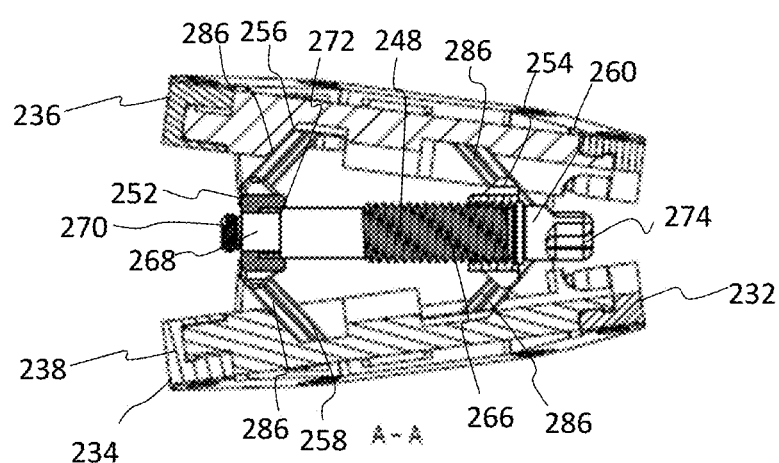
Figure 19A:
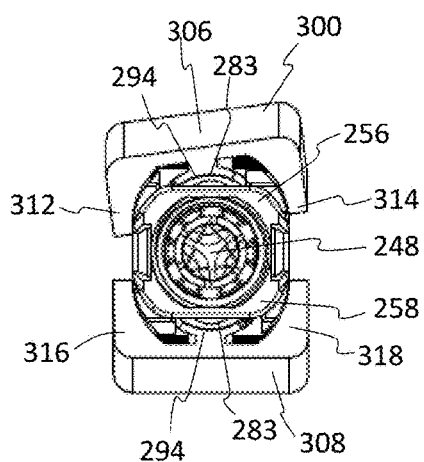
FIG. 19A-19D show rear, perspective, top, and side views, respectively, of an expandable fusion device according to another embodiment.
Figure 19B:
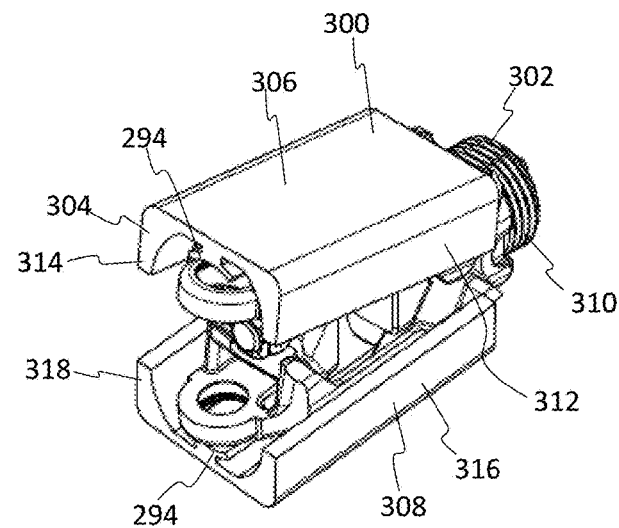
Figure 19C:
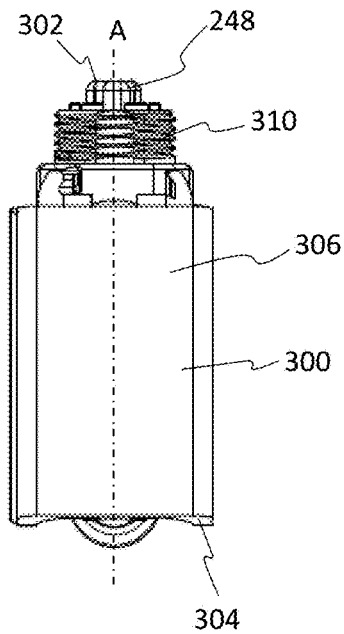
Figure 19D:
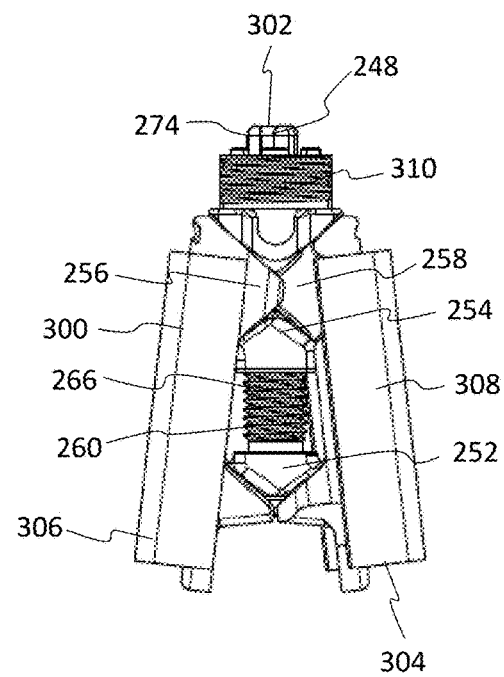

The actuator 248 may include a shaft 260 extending from a proximal end 262 to a distal end 264. The shaft 260 may include a threaded portion 266 and a non-threaded portion 268. In FIG. 17B, a cross-sectional view of the implant 230 is shown along line A-A from FIG. 17A in a widened orientation and collapsed in height. In FIG. 17C, a cross-sectional view of the implant 230 is shown along line A-A in a widened orientation and expanded in height. As best seen in FIG. 17C, the front driving ramp 252 is positioned on the non-threaded portion 268 of the actuator 248. The front driving ramp 252 may be located between a securing washer 270 and a shoulder 272 along the non-threaded portion 268. In this manner, the front driving ramp 252 is secured to the actuator shaft 248. The rear driving ramp 254 is positioned along the threaded portion 266 of the shaft 260 in order to move the rear ramp 254 when the shaft 260 is rotated. The rear ramp 254 is moveable along the length of the threaded portion 266 to move the upper and lower ramps 256, 258 and expand the implant 230. For example, as shown in FIG. 17B, the rear ramp 254 is positioned near a distal end of the threaded portion 266. As the implant 230 is expanded, as shown in FIG. 17C, the rear ramp 254 moves toward a proximal end of the threaded portion 266. As the actuator 248 moves forward, front ramp 252 may move forward and rear ramp 254 may move backward, thereby moving away from the front ramp 252, and expanding the implant 230 in height. The proximal end 262 of the actuator shaft 260 may include an instrument retention feature, such as a ribbed neck 274. The ribbed neck 274 may include knurled neck grips or other suitable engagement surfaces, which are configured to interface with a driver instrument to thereby rotate the actuator shaft 260.

The driving ramps 252, 254 engage with upper ramp 256 and lower ramp 258 to thereby move the upper and lower ramps 256, 258 outwardly in height. It will be appreciated that the lower ramp 258 is identical to the upper ramp 256 and the description for the upper ramp 256 herein applies equally to the lower ramp 258. The upper ramp 256 extends from a proximal end 276 to a distal end 278, which are configured to engage with the upper endplates 236. In particular, a first tab 280 may extend outwardly from the proximal end 276 of the ramp 256 and a second tab 282 may extend in the opposite direction outwardly from the distal end 278 of the ramp 256. A portion of the first and second tabs 280, 282 may be rounded about the longitudinal axis A of the implant 230. For example, a rounded portion 283 on the upper ramp 256 may include an upper surface configured to mate with the upper endplates 236 and the rounded portion 283 on the lower ramp 258 may include a lower surface configured to mate with the lower endplates 238. The rounded portions 283 may facilitate movement of the endplates 236 about the longitudinal axis A of the implant 230. The rounded portion 283 may be received in a mating rounded recess 294 defined within the rear-most link 243. A similar rounded mating interface may be provided within the opening 247 in the front-most link 245. In this manner, the upper endplate assembly 236 is configured to pivot about the longitudinal axis A so that the implant 230 can passively account for the mismatch of the oblique angle of insertion and the desired sagittal angle. Without this type of polyaxial joint, the endplates 236, 238 could dig into and/or tip the vertebral bodies 2 when implanted.

The upper ramp 256 includes an inner surface 284 configured to mate with the driving ramps 252, 254. The inner surface 284 may include one or more ramped surfaces 286, 288. In the embodiment shown, the inner surface 284 includes at least a first ramped surface 286 near the proximal end 276 of the upper ramp 256 and at least a second ramped surface 288 near the distal end 278 of the upper ramp 256. The first ramped surface 286 may include a first pair of ramped surfaces 286 and the second ramped surface 288 may include a second pair of ramped surfaces 288. The ramped surfaces 286, 288 may be angled continuous surfaces with a given angle of slope. The ramped surfaces 286, 288 may include male slide ramps or protruding ramps. The first and second ramped surfaces 286, 288 may be angled opposite to one another such that the ramped surfaces 286, 288 may face one another. For example, the first ramped surface 286 may have an apex near the proximal end 276 and the second ramped surface 288 may have an apex near the distal end 278 of the ramp 256. Although a specific arrangement of ramped surfaces 286, 288 is shown, it is envisioned that the number, location, and configuration of ramped surfaces 286, 288 may be modified or selected by one skilled in the art.

The driving ramps 252, 254 include one or more ramped surfaces 290, 292 configured to mate with the corresponding ramped surfaces 286, 288 of the upper and lower ramps 256, 258. For example, the rear driving ramp 254 may include one or more ramped surfaces 290 and front driving ramp 252 may include one or more ramped surfaces 292. The ramped surfaces 290, 292 may be angled continuous surfaces with a given angle of slope. The ramped surfaces 290, 292 may include female slide ramps or recessed ramps configured to receive the male ramped surfaces 286, 288 of the upper and lower ramps 256, 258. It will be appreciated that the male and female ramps may be reversed or may be otherwise configured to provide for slidable mating between the ramps. The first ramped surface 286 of the upper ramp 256 may be configured to slidably interface with the ramped surface 290 of the rear driving ramp 254. The second ramped surface 288 of the upper ramp 256 may be configured to slidably interface with the ramped surface 292 of the front driving ramp 252. In this manner, the individual driving ramps 252, 254 control the rate of expansion of the upper and lower ramps 256, 258, which thereby controls the expansion of the attached upper and lower endplate assemblies 236, 238.

As shown in FIGS. 18A-18C, implant 230 may be implanted from an oblique approach similar to implant 20. The spine may be accessed posteriorly. A cannula may be docked on the disc space through Kambin's triangle, or the anatomical area that is bordered by the disc space, exiting nerve root, and traversing nerve root. The approach may be oblique, for example, at about a 30° angle relative to a straight posterior access path. The expandable interbody 230 is inserted in the non-articulated, collapsed orientation. The expandable interbody 230 is actuated into the expanded footprint that fully maximizes surface contact area with the vertebral body 2. Then, the expandable interbody 230 is expanded in height to precisely restore normal spinal alignment and evenly distribute the load across the vertebral endplates. The passive longitudinal axis allows for the implant endplates 236, 238 to pivot to match the vertebral body endplate angles and minimize any edge loading.

Turning now to FIGS. 19A-20D, an expandable interbody fusion device or implant 300 according to another embodiment is shown. The expandable device 300 is similar to implant 230 but is only configured to expand in height. The implant 300 is configured to be inserted in a collapsed orientation, which defines its smallest height. Once inserted into the disc space, the implant 300 is expanded in height to an expanded orientation. Similar to implant 230, the implant 300 may be configured to pivot about the longitudinal axis A of the implant 300 so that it can passively account for the mismatch of the oblique angle of insertion and/or the desired sagittal angle.

As best seen in FIGS. 19A-19D, the implant 300 extends from a rear end or proximal end 302 configured to connect with an insertion instrument to a nose end or distal end 304 configured to be inserted first into the disc space. The proximal end 302 of the implant 300 may include an outer threaded portion 310 configured to threadedly mate with an insertion instrument.

The implant 300 includes a first or upper endplate 306 and a second or lower endplate 308, which are configured to engage with the adjacent vertebrae 2. The upper endplate 306 may include opposed side walls 312, 314 and lower endplate 308 may include opposed side walls 316, 318. The side walls 312, 314, 316, 318 may completely conceal or mostly conceal the internal expansion mechanism when the implant 300 is in the collapsed configuration. Although not shown, the endplates 306, 308 may have teeth or friction enhancing surfaces and/or one or more graft windows for receiving a graft material if desired.

The upper and lower endplates 306, 308 are mated with the upper and lower ramps 256, 258, respectively. The expansion mechanism works in the same manner as described for implant 230. The front and rear driving ramps 252, 254 slidably interface with the upper and lower ramps 256, 258. When the actuator 248 is rotated, the driving ramps 252, 254 force the upper and lower ramps 256, 258 away from one another, thereby expanding the height of the upper and lower endplates 306, 308. For example, when the actuator 248 moves forward, the front driving ramp 252 may move forward and the rear driving ramp 254 may move backward along the threaded portion 266 of the shaft 260 of the actuator 248. As the driving ramps 252, 254 move away from one another, the height of the implant 300 is increased.

The upper and lower endplates 306, 308 are able to passively pivot about the longitudinal axis A of the implant 300, such that the endplates 306, 308 are able to passively match the vertebral body endplate angles and minimize any edge loading. Similar to implant 230, the upper ramp 256 may include a rounded portion 283 along an upper surface configured to mate with the upper endplate 306 and a rounded portion 283 along a lower surface on the lower ramp 258 configured to mate with the lower endplate 308.

The rounded portion 283 may be received in a mating rounded recess 294 defined within the upper and lower endplates 306, 308. In this manner, the upper and lower endplates 306, 308 are configured to pivot about the longitudinal axis A so that the implant 300 can passively account for the mismatch of the oblique angle of insertion and the desired sagittal angle.

As shown in FIGS. 20A-20D, implant 300 may be implanted from an oblique approach similar to implants 20, 230. The spine may be accessed posteriorly. A cannula may be positioned on the disc space through Kambin's triangle, or the anatomical area that is bordered by the disc space, exiting nerve root, and traversing nerve root. The approach may be oblique, for example, at about a 30° angle relative to a straight posterior access. The expandable interbody 300 is inserted in the collapsed orientation. The expandable interbody 230 is then expanded in height to precisely restore normal spinal alignment. The passive longitudinal axis allows for the implant endplates 306, 308 to pivot to match the vertebral body endplate angles and minimize any edge loading.

The expandable fusion devices described herein may be manufactured from a number of biocompatible materials including, but not limited to, titanium, stainless steel, titanium alloys, non-titanium metallic alloys, polymeric materials, plastics, plastic composites, PEEK, ceramic, and elastic materials.

The features of the embodiments described herein may provide one or more of the following advantages. A small insertion profile, such as a 10 mm insertion width into the disc space, may reduce skin, fascia, muscle, and/or ligamentous disruption. A controlled lordosis may be achieved through placement of the interbody in an articulated position on the anterior apophyseal ring. The interbody may continuously increase lordosis during expansion of the interbody. A reduced endplate disruption may occur due to the expansion profile of the implant, and may reduce the need for traditional trialing of interbody implants which may contribute to endplate disruption. The implant may passively adapt to the endplate profiles to maximize load distribution and minimize edge loading and the associated subsidence. It will be appreciated that different or additional advantages may also be achieved based on the disclosure herein.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. An expandable implant comprising:
    an upper endplate assembly including a plurality of upper endplates;
    a lower endplate assembly including a plurality of lower endplates;
    an actuator assembly including a rotatable actuator having a shaft and a rotatable nut;
    a plurality of driving ramps including a front ramp, a mid-ramp, and a rear ramp positioned along the shaft of the actuator;
    an upper ramp connected to the upper endplate assembly and engaged with the plurality of driving ramps; and a lower ramp connected to the lower endplate assembly and engaged with the plurality of driving ramps, wherein the upper and lower endplate assemblies are configured to expand in width, and wherein rotation of the actuator and/or the nut causes movement of one or more of the driving ramps, thereby causing an expansion in height of the upper and lower endplate assemblies, wherein the shaft of the actuator includes a first threaded portion, a second threaded portion, and a non-threaded portion, wherein the front ramp is positioned on the non-threaded portion of the actuator, the mid-ramp is positioned on the first threaded portion, and the rear ramp is positioned on the second threaded portion.

2. The expandable implant of claim 1, wherein the plurality of upper endplates includes a first upper outer endplate, a second upper outer endplate, and a third upper central endplate positionable between the first and second upper outer endplates, and wherein the plurality of lower endplates includes a first lower outer endplate, a second lower outer endplate, and a third lower central endplate positionable between the first and second lower outer endplates.

3. The expandable implant of claim 2, wherein the upper and lower central endplates are configured to expand the respective upper and lower outer endplates outwardly, thereby expanding an overall width of the expandable implant.

4. The expandable implant of claim 2, wherein, for each pair of outer endplates, one of the outer endplates includes an elongate groove and the other outer endplate retains a pin configured to be received within the elongate groove, wherein when the outer endplates move outwardly, the pin is guided along a path of the elongate groove.

5. The expandable implant of claim 4, wherein the elongate groove is a linear groove that allows for a parallel expansion in width of the outer endplates.

6. The expandable implant of claim 2, wherein the central endplates are configured to slide between the respective outer endplates on one or more tracks.

7. The expandable implant of claim 6, wherein when the central endplates are advanced forward distally along the one or more tracks, the outer endplates expand in width.

8. The expandable implant of claim 1, wherein the first threaded portion has a smaller outer diameter and different handedness than the second threaded portion.

9. The expandable implant of claim 1, wherein the rotatable nut is configured to move the rear ramp independent of the mid-ramp the front ramp.

10. The expandable implant of claim 1, wherein the upper and lower endplate assemblies are configured to passively pivot about a longitudinal axis of the expandable implant.

11. An expandable implant comprising:

an upper endplate assembly including a plurality of upper endplates;

a lower endplate assembly including a plurality of lower endplates;

an actuator assembly including a rotatable actuator having a shaft and a rotatable nut;

a plurality of driving ramps including a front ramp, a mid-ramp, and a rear ramp positioned along the shaft of the actuator;

an upper ramp connected to the upper endplate assembly and engaged with the plurality of driving ramps; and a lower ramp connected to the lower endplate assembly and engaged with the plurality of driving ramps, wherein the upper and lower endplate assemblies are configured to expand in width, and wherein rotation of the actuator and/or the nut causes movement of one or more of the driving ramps, thereby causing an expansion in height of the upper and lower endplate assemblies, wherein the upper and lower endplate assemblies are configured to passively pivot about a longitudinal axis of the expandable implant.

* * * * *